US012600999B2

(12) United States Patent
Ueno et al.

(10) Patent No.: US 12,600,999 B2
(45) Date of Patent: Apr. 14, 2026

(54) PROTEIN CRYSTAL PRODUCTION METHOD AND CRYSTALLINE STRUCTURE ANALYSIS METHOD

(71) Applicant: Institute of Science Tokyo, Tokyo (JP)

(72) Inventors: Takafumi Ueno, Tokyo (JP); Satoshi Abe, Tokyo (JP); Mariko Kojima, Tokyo (JP)

(73) Assignee: Institute of Science Tokyo, Tokyo (JP)

( * ) Notice: Subject to any disclaimer, the term of this patent is extended or adjusted under 35 U.S.C. 154(b) by 785 days.

(21) Appl. No.: 17/800,397

(22) PCT Filed: Feb. 22, 2021

(86) PCT No.: PCT/JP2021/006607
§ 371 (c)(1),
(2) Date: Aug. 17, 2022

(87) PCT Pub. No.: WO2021/167104
PCT Pub. Date: Aug. 26, 2021

(65) Prior Publication Data
US 2023/0159975 A1 May 25, 2023

(30) Foreign Application Priority Data

Feb. 20, 2020 (JP) ................................. 2020-027386

(51) Int. Cl.
| *C12P 21/02* | (2006.01) |
| *C07K 14/005* | (2006.01) |
| *C12N 15/62* | (2006.01) |
| *C12N 15/70* | (2006.01) |

(52) U.S. Cl.
CPC ............ *C12P 21/02* (2013.01); *C07K 14/005* (2013.01); *C12N 15/62* (2013.01); *C12N 15/70* (2013.01); *C07K 2319/00* (2013.01); *C12N 2710/14122* (2013.01); *C12N 2710/14152* (2013.01); *C12N 2720/12022* (2013.01); *C12N 2720/12052* (2013.01); *C12N 2800/101* (2013.01); *C12N 2840/002* (2013.01)

(58) Field of Classification Search
CPC ...................................................... C12P 21/02
See application file for complete search history.

(56) References Cited

U.S. PATENT DOCUMENTS

2004/0059091 A1 3/2004 Ohta et al.

FOREIGN PATENT DOCUMENTS

| EP | 3330282 A1 | 6/2018 |
| JP | 2010520196 A | 6/2010 |
| JP | 2015159731 A | 9/2015 |
| JP | 2018033404 A | 3/2018 |
| WO | 2002036785 A1 | 5/2002 |

| WO | 2008105672 A1 | 9/2008 |
| WO | 2017074268 A1 | 5/2017 |
| WO | 2021025126 A1 | 2/2021 |

OTHER PUBLICATIONS

Abe et al., "Crystal Engineering of Self-Assembled porous protein materials in living cells," ACS Nano. 2017; 11:2410-19.
Abe et al., "Design of a confined environment using protein cages and crystals for the development of biohybrid materials," Chem Comm. 2016; 52:6496.
Ashida, "Introduction to Protein Crystallography," Journal of the Crystallographic Society of Japan. 1996; 38(6):378-88.
Baskaran et al., "An in cellulo-derived structure of PAK4 complex with its inhibitor Inka1," Nat. Commun. 2015; 6:8681.
Bintrim et al., "Insertional inactivation of genes encoding crystalline inclusion proteins of photorhabdus luminescens results mutants with pleiotropic phenotypes," J. Bacteriol. 1998; 180(5):1261-69.
Brandariz-Nunez et al., "Avian reovirus μNS protein forms homo-oligomeric inclusions in a microtubule-independent fashion, which involves specific regions of its C-terminal domain," J. Virol. 2010; 84(9):4289-4301.
Carmona et al., "Expression and crystallization of a Cry3Aa-Cry1Ac chimerical protein of bacillus thuringiensis," World J. Microbiol. Biotechnol. 1999; 15:455-63.
Chiu et al., "Structural basis for the enhancement of virulence viral spindles and their in vivo crystallization," Proc. Natl. Acad. USA. 2015; 112(13):3973-78.
Choudhary et al., "Engineered protein nano-compartments for targeted enzyme localization," PLOS One. 2012; 7(3):e33342.
Duszenko et al., "In vivo protein crystallization in combination with highly brilliant radiation sources offers novel opportunities for the structural analysis of post-translationally modified eukaryotic proteins," Acta Crystallogr. F. 2015; 71:929-37.
Duyvesteyn et al., "Towards in cellulo virus crystallography," Sci. Rep. 2018; 8:3771.
Echeverry et al., "Sequence analysis and expression of the polyhedrin gene of *Choristoneura fumiferana* cytoplasmic bolyhedrosis virus (CfCPV)," Gene. 1997; 198:399-406.
Gati et al., "Serial crystallography on in vivo microcrystals using synchrotron radiation," IUCrJ. 2014; 1:87-94.
Havemann et al., "PduA is a shell protein of polyhedral organelles involved in coenzyme B12-dependent degradation of 1,2-propanediol in salmonella enterica serovar typhimurium LT2," J. Bacteriol. 2002; 184(5):1253-61.
Heldt et al., "Structure of a trimeric bacterial microcompartment shell protein, EtuB, associated with ethanol utilization in Clostridium kluyveri," Biochem. J. 2009; 423:199-207.

(Continued)

*Primary Examiner* — Suzanne M Noakes
(74) *Attorney, Agent, or Firm* — Knobbe, Martens, Olson & Bear, LLP

(57) ABSTRACT

A production method for a crystal of a crystalline protein, the method including a step of inducing expression of a crystalline protein in *Escherichia coli* into which an expression construct of the crystalline protein has been introduced, and incubating the *Escherichia coli* for a predetermined time until a crystal of the crystalline protein is formed inside the *Escherichia coli*, and a crystal structure analysis method including a step of subjecting a crystal produced by the above-described production method to an X-ray crystal structure analysis together with the *Escherichia coli*, are useful as technologies for conveniently producing and analyzing a crystal of a protein.

4 Claims, 29 Drawing Sheets

Specification includes a Sequence Listing.

(56) References Cited

OTHER PUBLICATIONS

Hempstead et al., "Comparison of the three-dimensional structures of recombinant human H and horse L ferritins at high resolution," J. Mol. Biol. 1997; 268:424-48.

Ijiri et al., "Structure-based targeting of bioactive proteins cypovirus polyhedra and application to immobilized cytokines mammalian cell culture," Biomaterials. 2009; 30:4297-4308.

Kogure et al., "Optimization of intracellular protein crystallization," The Chemical Society of Japan. 2020; 100th, 4g1-12.

Koopmann et al., "In vivo protein crystallization opens routes in structural biology," Nature Methods. 2012; 9(3):259-62.

Lavallee et al., "Expression in *Escherichia coli* of the polyhedrin gene of bombyx mori cytoplasmic polyhedrosis Protein," Exp. Purif. 1993; 4:570-79.

Lemire et al., "Phage-Based Applications in Synthetic Biology," Annual Reviews of Virology. 2018; 5:453-76.

McDade, "Developing an in cellulo carrier-driven crystallization system using cry1Ac from bacillus thuringiensis," Master Thesis, University of Calgary. 2019; i-xiii:1-146.

Mori et al., "Application of insect virus polyhedra to protein nanocontainers," NSTI—Nanotech. 2010; 3:254-57.

Mori et al., "Cytoplasmic polyhedrosis virus and polyhedrin," virus. 1998; 48(1):81-88.

Mori, "Structural analysis of polyhedrosis produced silk moth cytoplasmic polyhedrosis virus and application of polyhedrosis," Sanshi-Konchu Biotec. 2007; 76(3):181-88.

Nöel et al., "Purification and characterization of protein nanotubes assembled from a single bacterial microcompartment shell subunit," Adv. Mater. Interfaces. 2016; 3:1500295.

Oeda et al., "Formation of crystals of the insecticidal proteins of bacillus thuringiensis subsp.aizawai IPL7 in *Escherichia coli*," J. Bacteriol. 1989; 171(6):3568-71.

Pang et al., "Structural insights into higher order assembly function of the bacterial microcompartment protein PduA," J. Biol. Chem. 2014; 289(32):22377-84.

Parsons et al., "Synthesis of empty bacterial microcompartments, Directed Organelle Protein Incorporation, and evidence of filament-associated organelle movement," Mol. Cell. 2010; 38:305-15.

Parsons et al., "Biochemical and structural insights bacterial organelle form and biogenesis," J. Biol. Chem. 2008; 283(21):14366-75.

Petoukhov et al., "Crystallization in starved *E. coli* cells studied by synchrotron small-angle scattering," FEBS Open. 2018; 8(suppl. S1):438, p. 19-043-Mon.

Pitts et al., "Structural insight into the clostridium difficile ethanolamine utilisation microcompartment," PLOS One. 2012; 7(10):e48360.

Schönherr et al., "Protein crystallization in living cells," Biol. Chem. 2018; 399(7):751-72.

Schönherr et al., "Real-time investigation of dynamic protein crystalization in living cells," Struct. Dyn. 2015; 2:041712.

Seo et al., "Baculoviral polyhedrin as a novel fusion partner formation of inclusion body in *Escherichia coli*," Biotechnol. 2003; 84(4):467-73.

Seo et al., "Baculoviral polyhedrin-bacillus thuringiensis fusion protein: A protein-based bio-insecticide expressed in *Escherichia coli*," Biotechnol. Bioeng. 2005; 92(2):166-72.

Shtykova et al., "Phenomenon of DNA preservation in stress induced cells: structural peculiarities of biocrystallization processes in vivo and in vitro," revealed by SAXS, FEBS Open Bio. 2019; 9(suppl. 1):37, ShT-21-1.

Takeda et al., "Cloning, expression and characterization of horse L-ferritin in *Escherichia coli*," Biochim. Biophys. Acta. 1993; 1174:218-20.

Van Der Linden et al., "In vivo crystal formation in *Escherichia coli* of an over-expressed soluble form of penicillin-binding protein 5," FEMS Microbiol. Lett. 1992; 99:117-24.

"Iwanami Physics and Chemistry Dictionary," 5th Edition. 2003; p. 415.

International Search Report for PCT Application No. PCT/JP2021/006607 mailed Apr. 6, 2021.

Written Opinion for PCT Application No. PCT/JP2021/006607 mailed Nov. 22, 2021.

International Preliminary Report on Patentability for PCT Application No. PCT/JP2021/006607 mailed Feb. 8, 2022.

CPV

NPV

CPV

NPV

N29S

Δ3

Δ38

30°C

30°C

30°C

37°C

37°C

37°C

Resolution: 1.8 Å

Space group: I23

Cell length (Å)
$a = b = c$   103.5

Δ3(192-194 DELETED)

RESOLUTION : 2.3 Å

Δ38 (67-104 DELETED)

RESOLUTION : 2.5 Å

3.6 nm 3.0 nm

THALIDOMIDE-BINDING DOMAIN

TBD-PhM

PhM-TBD

FRAGMENT 1 : M1-S114

FIG. 16B
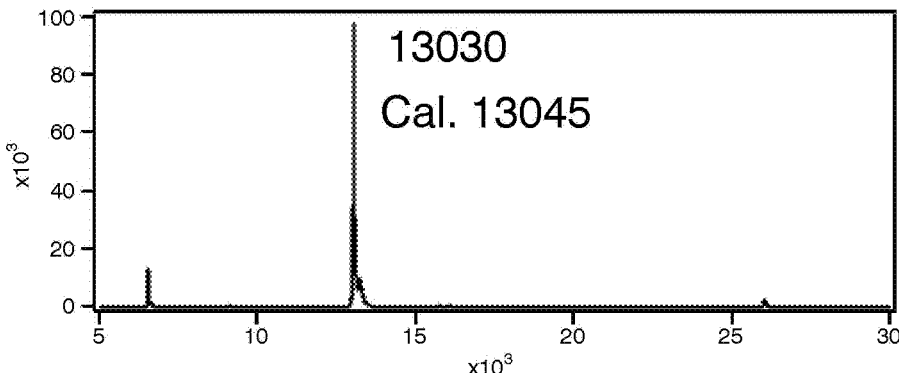
FIG. 16C
FRAGMENT 2 : M1-R155
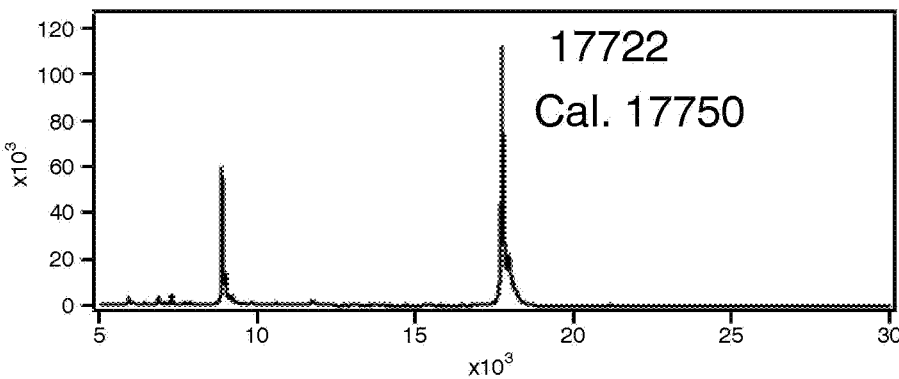
FIG. 16D

FRAGMENT 3 : S116-Q248

FRAGMENT 4 : K58-Q248

SEQUENCE LISTING

<160> NUMBER OF SEQ ID NOS: 27

<210> SEQ ID NO 1
<211> LENGTH: 210
<212> TYPE: PRT
<213> ORGANISM: Artificial Sequence
<220> FEATURE:
<223> OTHER INFORMATION: Synthesized protein derived from cytoplasmic
       polyhedrosis virus

<400> SEQUENCE: 1

```
Met Ala Asp Val Ala Gly Thr Ser Asn Arg Asp Phe Arg Gly Arg Glu
1               5                   10                  15

Gln Arg Leu Phe Asn Ser Glu Gln Tyr Asn Tyr Asn Asn Ser Leu Asn
            20                  25                  30

Gly Glu Val Ser Val Trp Val Tyr Ala Tyr Tyr Ser Asp Gly Ser Val
        35                  40                  45

Leu Val Ile Asn Lys Asn Ser Gln Tyr Lys Val Gly Ile Ser Glu Thr
    50                  55                  60

Phe Lys Lys Pro Arg Ala Ile Gln Ile Ile Phe Ser Pro Ser Val Asn
65                  70                  75                  80

Val Arg Thr Ile Lys Met Ala Lys Gly Asn Ala Val Ser Val Pro Asp
                85                  90                  95

Glu Tyr Leu Gln Arg Ser His Pro Trp Glu Ala Thr Gly Ile Lys Tyr
            100                 105                 110

Arg Lys Ile Lys Arg Asp Gly Glu Ile Val Gly Tyr Ser His Tyr Phe
        115                 120                 125

Glu Leu Pro His Glu Tyr Asn Ser Ile Ser Leu Ala Val Ser Gly Val
    130                 135                 140
```

-continued

```
His Lys Asn Pro Ser Ser Tyr Asn Val Gly Ser Ala His Asn Val Met
145                 150                 155                 160

Asp Val Phe Gln Ser Cys Asp Leu Ala Leu Arg Phe Cys Asn Arg Tyr
                165                 170                 175

Trp Ala Glu Leu Glu Leu Val Asn His Tyr Ile Ser Pro Asn Ala Tyr
            180                 185                 190

Pro Tyr Leu Asp Ile Asn Asn His Ser Tyr Gly Val Ala Leu Ser Asn
        195                 200                 205

Arg Gln
    210

<210> SEQ ID NO 2
<211> LENGTH: 248
<212> TYPE: PRT
<213> ORGANISM: Cytoplasmic polyhedrosis virus

<400> SEQUENCE: 2

Met Ala Asp Val Ala Gly Thr Ser Asn Arg Asp Phe Arg Gly Arg Glu
1               5                   10                  15

Gln Arg Leu Phe Asn Ser Glu Gln Tyr Asn Tyr Asn Asn Ser Leu Asn
            20                  25                  30

Gly Glu Val Ser Val Trp Val Tyr Ala Tyr Tyr Ser Asp Gly Ser Val
            35                  40                  45

Leu Val Ile Asn Lys Asn Ser Gln Tyr Lys Val Gly Ile Ser Glu Thr
        50                  55                  60

Phe Lys Ala Leu Lys Glu Tyr Arg Glu Gly Gln His Asn Asp Ser Tyr
65                  70                  75                  80

Asp Glu Tyr Glu Val Asn Gln Ser Ile Tyr Tyr Pro Asn Gly Gly Asp
                85                  90                  95

Ala Arg Lys Phe His Ser Asn Ala Lys Pro Arg Ala Ile Gln Ile Ile
            100                 105                 110

Phe Ser Pro Ser Val Asn Val Arg Thr Ile Lys Met Ala Lys Gly Asn
            115                 120                 125

Ala Val Ser Val Pro Asp Glu Tyr Leu Gln Arg Ser His Pro Trp Glu
        130                 135                 140

Ala Thr Gly Ile Lys Tyr Arg Lys Ile Lys Arg Asp Gly Glu Ile Val
145                 150                 155                 160

Gly Tyr Ser His Tyr Phe Glu Leu Pro His Glu Tyr Asn Ser Ile Ser
                165                 170                 175

Leu Ala Val Ser Gly Val His Lys Asn Pro Ser Ser Tyr Asn Val Gly
            180                 185                 190

Ser Ala His Asn Val Met Asp Val Phe Gln Ser Cys Asp Leu Ala Leu
        195                 200                 205

Arg Phe Cys Asn Arg Tyr Trp Ala Glu Leu Glu Leu Val Asn His Tyr
        210                 215                 220

Ile Ser Pro Asn Ala Tyr Pro Tyr Leu Asp Ile Asn Asn His Ser Tyr
225                 230                 235                 240

Gly Val Ala Leu Ser Asn Arg Gln
                245

<210> SEQ ID NO 3
<211> LENGTH: 248
<212> TYPE: PRT
<213> ORGANISM: Nuclear polyhedrosis virus

<400> SEQUENCE: 3
```

```
Met Ala Asp Val Ala Gly Thr Ser Asn Arg Asp Phe Arg Gly Arg Glu
1               5                   10                  15

Gln Arg Leu Phe Asn Ser Glu Gln Tyr Asn Tyr Asn Asn Ser Leu Asn
            20                  25                  30

Gly Glu Val Ser Val Trp Val Tyr Ala Tyr Tyr Ser Asp Gly Ser Val
            35                  40                  45

Leu Val Ile Asn Lys Asn Ser Gln Tyr Lys Val Gly Ile Ser Glu Thr
    50                  55                  60

Phe Lys Ala Leu Lys Glu Tyr Arg Glu Gly Gln His Asn Asp Ser Tyr
65                  70                  75                  80

Asp Glu Tyr Glu Val Asn Gln Ser Ile Tyr Tyr Pro Asn Gly Gly Asp
                85                  90                  95

Ala Arg Lys Phe His Ser Asn Ala Lys Pro Arg Ala Ile Gln Ile Ile
            100                 105                 110

Phe Ser Pro Ser Val Asn Val Arg Thr Ile Lys Met Ala Lys Gly Asn
            115                 120                 125

Ala Val Ser Val Pro Asp Glu Tyr Leu Gln Arg Ser His Pro Trp Glu
    130                 135                 140

Ala Thr Gly Ile Lys Tyr Arg Lys Ile Lys Arg Asp Gly Glu Ile Val
145                 150                 155                 160

Gly Tyr Ser His Tyr Phe Glu Leu Pro His Glu Tyr Asn Ser Ile Ser
                165                 170                 175

Leu Ala Val Ser Gly Val His Lys Asn Pro Ser Ser Tyr Asn Val Gly
            180                 185                 190

Ser Ala His Asn Val Met Asp Val Phe Gln Ser Cys Asp Leu Ala Leu
            195                 200                 205

Arg Phe Cys Asn Arg Tyr Trp Ala Glu Leu Glu Leu Val Asn His Tyr
    210                 215                 220

Ile Ser Pro Asn Ala Tyr Pro Tyr Leu Asp Ile Asn Asn His Ser Tyr
225                 230                 235                 240

Gly Val Ala Leu Ser Asn Arg Gln
                245
```

<210> SEQ ID NO 4
<211> LENGTH: 340
<212> TYPE: PRT
<213> ORGANISM: Trypanosoma brucei

<400> SEQUENCE: 4

```
Met His Leu Met Arg Ala Cys Ile Thr Phe Cys Ile Ala Ser Thr Ala
1               5                   10                  15

Val Val Ala Val Asn Ala Ala Leu Val Ala Glu Asp Ala Pro Val Leu
            20                  25                  30

Ser Lys Ala Phe Val Asp Arg Val Asn Arg Leu Asn Arg Gly Ile Trp
            35                  40                  45

Lys Ala Lys Tyr Asp Gly Val Met Gln Asn Ile Thr Leu Arg Glu Ala
    50                  55                  60

Lys Arg Leu Asn Gly Val Ile Lys Lys Asn Asn Asn Ala Ser Ile Leu
65                  70                  75                  80

Pro Lys Arg Arg Phe Thr Glu Glu Glu Ala Arg Ala Pro Leu Pro Ser
                85                  90                  95

Ser Phe Asp Ser Ala Glu Ala Trp Pro Asn Cys Pro Thr Ile Pro Gln
            100                 105                 110

Ile Ala Asp Gln Ser Ala Cys Gly Ser Cys Trp Ala Val Ala Ala Ala
            115                 120                 125
```

```
Ser Ala Met Ser Asp Arg Phe Cys Thr Met Gly Gly Val Gln Asp Val
    130                 135             140

His Ile Ser Ala Gly Asp Leu Leu Ala Cys Cys Ser Asp Cys Gly Asp
145                 150             155                 160

Gly Cys Asn Gly Gly Asp Pro Asp Arg Ala Trp Ala Tyr Phe Ser Ser
                165             170             175

Thr Gly Leu Val Ser Asp Tyr Cys Gln Pro Tyr Pro Phe Pro His Cys
            180             185             190

Ser His His Ser Lys Ser Lys Asn Gly Tyr Pro Pro Cys Ser Gln Phe
            195             200             205

Asn Phe Asp Thr Pro Lys Cys Asn Tyr Thr Cys Asp Asp Pro Thr Ile
    210             215             220

Pro Val Val Asn Tyr Arg Ser Trp Thr Ser Tyr Ala Leu Gln Gly Glu
225             230             235             240

Asp Asp Tyr Met Arg Glu Leu Phe Phe Arg Gly Pro Phe Glu Val Ala
            245             250             255

Phe Asp Val Tyr Glu Asp Phe Ile Ala Tyr Asn Ser Gly Val Tyr His
            260             265             270

His Val Ser Gly Gln Tyr Leu Gly Gly His Ala Val Arg Leu Val Gly
            275             280             285

Trp Gly Thr Ser Asn Gly Val Pro Tyr Trp Lys Ile Ala Asn Ser Trp
    290             295             300

Asn Thr Glu Trp Gly Met Asp Gly Tyr Phe Leu Ile Arg Arg Gly Ser
305             310             315             320

Ser Glu Cys Gly Ile Glu Asp Gly Gly Ser Ala Gly Ile Pro Leu Ala
            325             330             335

Pro Asn Thr Ala
            340

<210> SEQ ID NO 5
<211> LENGTH: 175
<212> TYPE: PRT
<213> ORGANISM: Equus caballus

<400> SEQUENCE: 5

Met Ser Ser Gln Ile Arg Gln Asn Tyr Ser Thr Glu Val Glu Ala Ala
1               5               10              15

Val Asn Arg Leu Val Asn Leu Tyr Leu Arg Ala Ser Tyr Thr Tyr Leu
            20              25              30

Ser Leu Gly Phe Tyr Phe Asp Arg Asp Asp Val Ala Leu Glu Gly Val
        35              40              45

Cys His Phe Phe Arg Glu Leu Ala Glu Glu Lys Arg Glu Gly Ala Glu
    50              55              60

Arg Leu Leu Lys Met Gln Asn Gln Arg Gly Gly Arg Ala Leu Phe Gln
65              70              75              80

Asp Leu Gln Lys Pro Ser Gln Asp Glu Trp Gly Thr Thr Leu Asp Ala
            85              90              95

Met Lys Ala Ala Ile Val Leu Glu Lys Ser Leu Asn Gln Ala Leu Leu
            100             105             110

Asp Leu His Ala Leu Gly Ser Ala Gln Ala Asp Pro His Leu Cys Asp
        115             120             125

Phe Leu Glu Ser His Phe Leu Asp Glu Glu Val Lys Leu Ile Lys Lys
    130             135             140

Met Gly Asp His Leu Thr Asn Ile Gln Arg Leu Val Gly Ser Gln Ala
```

```
145              150              155              160

Gly Leu Gly Glu Tyr Leu Phe Glu Arg Leu Thr Leu Lys His Asp
              165              170              175
```

<210> SEQ ID NO 6
<211> LENGTH: 175
<212> TYPE: PRT
<213> ORGANISM: Homo sapiens

<400> SEQUENCE: 6

```
Met Ser Ser Gln Ile Arg Gln Asn Tyr Ser Thr Asp Val Glu Ala Ala
1               5              10              15

Val Asn Ser Leu Val Asn Leu Tyr Leu Gln Ala Ser Tyr Thr Tyr Leu
              20              25              30

Ser Leu Gly Phe Tyr Phe Asp Arg Asp Asp Val Ala Leu Glu Gly Val
          35              40              45

Ser His Phe Phe Arg Glu Leu Ala Glu Glu Lys Arg Glu Gly Tyr Glu
      50              55              60

Arg Leu Leu Lys Met Gln Asn Gln Arg Gly Gly Arg Ala Leu Phe Gln
65              70              75              80

Asp Ile Lys Lys Pro Ala Glu Asp Glu Trp Gly Lys Thr Pro Asp Ala
              85              90              95

Met Lys Ala Ala Met Ala Leu Glu Lys Lys Leu Asn Gln Ala Leu Leu
          100             105             110

Asp Leu His Ala Leu Gly Ser Ala Arg Thr Asp Pro His Leu Cys Asp
          115             120             125

Phe Leu Glu Thr His Phe Leu Asp Glu Glu Val Lys Leu Ile Lys Lys
      130             135             140

Met Gly Asp His Leu Thr Asn Leu His Arg Leu Gly Gly Pro Glu Ala
145             150             155             160

Gly Leu Gly Glu Tyr Leu Phe Glu Arg Leu Thr Leu Lys His Asp
              165             170             175
```

<210> SEQ ID NO 7
<211> LENGTH: 167
<212> TYPE: PRT
<213> ORGANISM: Escherichia coli

<400> SEQUENCE: 7

```
Met Ser Thr Ala Lys Leu Val Lys Ser Lys Ala Thr Asn Leu Leu Tyr
1               5              10              15

Thr Arg Asn Asp Val Ser Asp Ser Glu Lys Lys Ala Thr Val Glu Leu
              20              25              30

Leu Asn Arg Gln Val Ile Gln Phe Ile Asp Leu Ser Leu Ile Thr Lys
          35              40              45

Gln Ala His Trp Asn Met Arg Gly Ala Asn Phe Ile Ala Val His Glu
      50              55              60

Met Leu Asp Gly Phe Arg Thr Ala Leu Ile Asp His Leu Asp Thr Met
65              70              75              80

Ala Glu Arg Ala Val Gln Leu Gly Gly Val Ala Leu Gly Thr Thr Gln
              85              90              95

Val Ile Asn Ser Lys Thr Pro Leu Lys Ser Tyr Pro Leu Asp Ile His
          100             105             110

Asn Val Gln Asp His Leu Lys Glu Leu Ala Asp Arg Tyr Ala Ile Val
          115             120             125

Ala Asn Asp Val Arg Lys Ala Ile Gly Glu Ala Lys Asp Asp Asp Thr
```

```
            130                 135                 140
Ala Asp Ile Leu Thr Ala Ala Ser Arg Asp Leu Asp Lys Phe Leu Trp
145                 150                 155                 160

Phe Ile Glu Cys Asn Ile Glu
                165

<210> SEQ ID NO 8
<211> LENGTH: 548
<212> TYPE: PRT
<213> ORGANISM: Luciola mingrelica

<400> SEQUENCE: 8

Met Glu Met Glu Lys Glu Glu Asn Val Val Tyr Gly Pro Leu Pro Phe
1               5                   10                  15

Tyr Pro Ile Glu Glu Gly Ser Ala Gly Ile Gln Leu His Lys Tyr Met
            20                  25                  30

His Gln Tyr Ala Lys Leu Gly Ala Ile Ala Phe Ser Asn Ala Leu Thr
        35                  40                  45

Gly Val Asp Ile Ser Tyr Gln Glu Tyr Phe Asp Ile Thr Cys Arg Leu
    50                  55                  60

Ala Glu Ala Met Lys Asn Phe Gly Met Lys Pro Glu Glu His Ile Ala
65                  70                  75                  80

Leu Cys Ser Glu Asn Cys Glu Glu Phe Phe Ile Pro Val Leu Ala Gly
                85                  90                  95

Leu Tyr Ile Gly Val Ala Val Ala Pro Thr Asn Glu Ile Tyr Thr Leu
                100                 105                 110

Arg Glu Leu Asn His Ser Leu Gly Ile Ala Gln Pro Thr Ile Val Phe
            115                 120                 125

Ser Ser Arg Lys Gly Leu Pro Lys Val Leu Glu Val Gln Lys Thr Val
    130                 135                 140

Thr Cys Ile Lys Lys Ile Val Ile Leu Asp Ser Lys Val Asn Phe Gly
145                 150                 155                 160

Gly His Asp Cys Met Glu Thr Phe Ile Lys Lys His Val Glu Leu Gly
                165                 170                 175

Phe Gln Pro Ser Ser Phe Val Pro Ile Asp Val Lys Asn Arg Lys Gln
                180                 185                 190

His Val Ala Leu Leu Met Asn Ser Ser Gly Ser Thr Gly Leu Pro Lys
            195                 200                 205

Gly Val Arg Ile Thr His Glu Gly Ala Val Thr Arg Phe Ser His Ala
    210                 215                 220

Lys Asp Pro Ile Tyr Gly Asn Gln Val Ser Pro Gly Thr Ala Ile Leu
225                 230                 235                 240

Thr Val Val Pro Phe His His Gly Phe Gly Met Phe Thr Thr Leu Gly
                245                 250                 255

Tyr Phe Ala Cys Gly Tyr Arg Val Val Met Leu Thr Lys Phe Asp Glu
                260                 265                 270

Glu Leu Phe Leu Arg Thr Leu Gln Asp Tyr Lys Cys Thr Ser Val Ile
            275                 280                 285

Leu Val Pro Thr Leu Phe Ala Ile Leu Asn Lys Ser Glu Leu Ile Asp
    290                 295                 300

Lys Phe Asp Leu Ser Asn Leu Thr Glu Ile Ala Ser Gly Gly Ala Pro
305                 310                 315                 320

Leu Ala Lys Glu Val Gly Glu Ala Val Ala Arg Arg Phe Asn Leu Pro
                325                 330                 335
```

-continued

```
Gly Val Arg Gln Gly Tyr Gly Leu Thr Glu Thr Thr Ser Ala Phe Ile
            340                 345                 350

Ile Thr Pro Glu Gly Asp Asp Lys Pro Gly Ala Ser Gly Lys Val Val
            355                 360                 365

Pro Leu Phe Lys Val Lys Val Ile Asp Leu Asp Thr Lys Lys Thr Leu
        370                 375                 380

Gly Val Asn Arg Arg Gly Glu Ile Cys Val Lys Gly Pro Ser Leu Met
    385                 390                 395                 400

Leu Gly Tyr Ser Asn Asn Pro Glu Ala Thr Arg Glu Thr Ile Asp Glu
                405                 410                 415

Glu Gly Trp Leu His Thr Gly Asp Ile Gly Tyr Tyr Asp Glu Asp Glu
            420                 425                 430

His Phe Phe Ile Val Asp Arg Leu Lys Ser Leu Ile Lys Tyr Lys Gly
        435                 440                 445

Tyr Gln Val Pro Pro Ala Glu Leu Glu Ser Val Leu Leu Gln His Pro
    450                 455                 460

Asn Ile Phe Asp Ala Gly Val Ala Gly Val Pro Asp Pro Asp Ala Gly
465                 470                 475                 480

Glu Leu Pro Gly Ala Val Val Val Met Glu Lys Gly Lys Thr Met Thr
                485                 490                 495

Glu Lys Glu Ile Val Asp Tyr Val Asn Ser Gln Val Val Asn His Lys
            500                 505                 510

Arg Leu Arg Gly Gly Val Arg Phe Val Asp Glu Val Pro Lys Gly Leu
        515                 520                 525

Thr Gly Lys Ile Asp Ala Lys Val Ile Arg Glu Ile Leu Lys Lys Pro
    530                 535                 540

Gln Ala Lys Met
545

<210> SEQ ID NO 9
<211> LENGTH: 311
<212> TYPE: PRT
<213> ORGANISM: Renilla reniformis

<400> SEQUENCE: 9

Met Thr Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Ala Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Cys Leu Ala Phe His
        115                 120                 125

Tyr Ser Tyr Glu His Gln Asp Lys Ile Lys Ala Ile Val His Ala Glu
    130                 135                 140

Ser Val Val Asp Val Ile Glu Ser Trp Asp Glu Trp Pro Asp Ile Glu
145                 150                 155                 160
```

-continued

```
Glu Asp Ile Ala Leu Ile Lys Ser Glu Glu Gly Lys Met Val Leu
            165             170             175

Glu Asn Asn Phe Phe Val Glu Thr Met Leu Pro Ser Lys Ile Met Arg
            180             185             190

Lys Leu Glu Pro Glu Glu Phe Ala Ala Tyr Leu Glu Pro Phe Lys Glu
            195             200             205

Lys Gly Glu Val Arg Arg Pro Thr Leu Ser Trp Pro Arg Glu Ile Pro
    210             215             220

Leu Val Lys Gly Gly Lys Pro Asp Val Val Gln Ile Val Arg Asn Tyr
225             230             235             240

Asn Ala Tyr Leu Arg Ala Ser Asp Asp Leu Pro Lys Met Phe Ile Glu
            245             250             255

Ser Asp Pro Gly Phe Phe Ser Asn Ala Ile Val Glu Gly Ala Lys Lys
            260             265             270

Phe Pro Asn Thr Glu Phe Val Lys Val Lys Gly Leu His Phe Ser Gln
            275             280             285

Glu Asp Ala Pro Asp Glu Met Gly Lys Tyr Ile Lys Ser Phe Val Glu
    290             295             300

Arg Val Leu Lys Asn Glu Gln
305             310

<210> SEQ ID NO 10
<211> LENGTH: 635
<212> TYPE: PRT
<213> ORGANISM: Avian orthoreovirus

<400> SEQUENCE: 10

Met Ala Ser Thr Lys Trp Gly Asp Lys Pro Met Ser Leu Ser Met Ser
1               5               10              15

His Asp Gly Ser Ser Ile Arg Ser Ala Ala Ser Gln Phe Leu Ser Val
            20              25              30

Pro Leu Ser His Ser Thr Pro Ile Pro Pro Gln Arg Lys Thr Val Leu
            35              40              45

Leu Lys Phe Met Ile Gly Asp Asp Leu Val Thr Val Gln Gly Ala Leu
    50              55              60

Ala Pro Phe Asp Glu Tyr Trp Tyr Asp Asn Gln Pro Leu Leu Ala Gln
65              70              75              80

Ala Val Glu Met Leu Ala Ser Glu Asp Arg Leu Arg Gln Phe Glu His
            85              90              95

Tyr Glu Lys Phe Leu Leu Lys Lys Gly His Gln Ile Ala Glu Ile Met
            100             105             110

Asn Arg Leu Arg Leu Phe Phe Thr Asp Val Leu Lys Val Lys Met Glu
            115             120             125

Ala Glu Ala Leu Pro Ala Leu Ala Gln Tyr Leu Met Val Gly Thr Leu
    130             135             140

Glu Ala Val Ser Thr Ala His Ser Pro Asp Ala Cys Val Pro Val Thr
145             150             155             160

Ser Lys Val Val Thr Lys Gln Gln Thr Ile Ala Lys Ser Pro Gly Arg
            165             170             175

Leu Asp Glu Glu Glu Tyr Asn Val Ile Arg Ser Arg Phe Leu Thr His
            180             185             190

Glu Val Phe Asp Leu Thr Ser Asp Leu Pro Gly Val Gln Pro Phe Met
            195             200             205

Asp Met Tyr Tyr Ala Thr Val Pro Arg Ala Asp Ser Thr Gly Trp Cys
```

```
        210              215              220

Val Tyr Arg Arg Lys Gly Leu Leu Ile His Ser Pro Asp Glu Gln Phe
225              230              235              240

Ser Asp Leu Thr Ile Phe Ser Thr Arg Leu Thr Ala Ser His Glu Leu
                 245              250              255

Gln Leu Val Ala Gly Asp Val Val Val Ala Cys Phe Asp Leu Met Asp
                 260              265              270

Val Ser Asp Ile Ala Pro Ser His His Ala Ser Val Gln Glu Glu Arg
             275              280              285

Thr Leu Gly Thr Ser Lys Tyr Ser Asn Ile Thr Ala Asn Asp His Pro
             290              295              300

Leu Val Phe Phe Ser Pro Ser Ala Leu Arg Trp Ala Ile Asp His Ala
305              310              315              320

Cys Thr Asp Ser Leu Val Ser Thr Arg Asn Ile Arg Val Cys Val Gly
                 325              330              335

Ile Asp Pro Leu Val Thr Arg Trp Thr Arg Asp Gly Val Gln Glu Ala
                 340              345              350

Ala Ile Leu Met Asp Asp Lys Leu Pro Ser Ala Gly Arg Ala Arg Met
             355              360              365

Ala Leu Arg Thr Leu Leu Leu Ala Arg Arg Ser Pro Met Pro Ser Phe
             370              375              380

Leu Leu Gly Ala Leu Lys Gln Ser Gly Gly Gln Leu Leu Glu His Tyr
385              390              395              400

Arg Cys Asp Ala Ala Asn Arg Tyr Gly Ser Pro Thr Val Pro Met Ser
             405              410              415

His Pro Pro Pro Cys Ser Lys Cys Pro Glu Leu Lys Glu Gln Ile Thr
             420              425              430

Lys Leu Ser Ser Ser Pro Thr Pro Lys Ile Asp Ser Thr Thr Gly Pro
             435              440              445

Ala Ala Leu Leu Ser Lys Ile Ser Asp Leu Gln Arg Ala Asn Arg Glu
             450              455              460

Leu Ser Leu Lys Leu Val Asp Met Gln Pro Ala Arg Glu Asp His Leu
465              470              475              480

Leu Ser Tyr Leu Asn Glu His Val Cys Val Asn Ala Arg Asp His Glu
                 485              490              495

Lys Gly Leu Leu Ser Arg Cys Asn Val Ser Asn Glu Ser Ile Ser Ser
             500              505              510

Ile Leu Asp Gln Arg Met Lys Asn Arg Glu Arg Phe Glu Thr Arg Leu
             515              520              525

Arg His Glu Ala Ser Ala Glu Trp Glu Pro Arg Val Glu Ala Leu Asn
             530              535              540

Gln Glu Leu Ala Lys Ala Arg Val Glu Gln Gln Asp Met Met Thr Gln
545              550              555              560

Ser Leu Gln Tyr Leu Asn Glu Arg Asp Glu Leu Leu His Glu Val Asp
                 565              570              575

Glu Leu Lys Arg Glu Leu Thr Thr Leu Arg Ala Ala Asn Val Arg Leu
             580              585              590

Asn Ala Asp Asn His Arg Met Ser Arg Ala Thr Arg Val Gly Asp Ala
             595              600              605

Phe Val Ser Asp Ile Glu Pro Leu Pro Ser Gly Ile Pro Gly Glu Ser
             610              615              620

Lys Pro Ser Met Glu Glu Leu Val Asp Asp Leu
625              630              635
```

```
<210> SEQ ID NO 11
<211> LENGTH: 387
<212> TYPE: PRT
<213> ORGANISM: Unknown
<220> FEATURE:
<223> OTHER INFORMATION: unidentified entomopoxvirus

<400> SEQUENCE: 11

Met Phe Ile Lys Ile Leu Pro Ile Leu Ile Leu Phe Leu Asp Tyr Val
1               5                   10                  15

Ser Gly His Gly Tyr Ile Thr Phe Pro Ile Ala Arg Gln Arg Arg Cys
                20                  25                  30

Asn Val Gln Gly Gly Phe Trp Trp Pro Pro Gly Gly Ser Gly Ile Pro
                35                  40                  45

Asp Pro Met Cys Arg Ala Ala Tyr Gln Asn Val Tyr Asn Lys Val Leu
        50                  55                  60

Gln Gln Gly Gly Thr Ile Asp Gln Ala Ala Ser Ala Ala Gln Tyr Met
65                  70                  75                  80

Phe Gln Gln Asp Asn Glu Tyr Ala Ala Leu Ala Gly Pro Asn Tyr Leu
                85                  90                  95

Asp Gln Asn His Ile Arg Asn Asn Val Val Pro Asn Tyr Leu Cys Ala
                100                 105                 110

Ala His Ala Thr Thr Trp Arg Ile Arg Pro Phe Gly Asp Lys Thr Gly
                115                 120                 125

Met Asp Val Ser Gly Ser Trp Thr Pro Thr Val Ile Pro Leu Gln Asp
        130                 135                 140

Asn Thr Val Ser Thr Val Pro Ile Glu Phe Glu Phe Cys Pro Thr Ala
145                 150                 155                 160

Ile His Glu Pro Ser Phe Phe Glu Ile Tyr Ile Thr Val Pro Ser Phe
                165                 170                 175

Asn Val Tyr Thr Asp Gln Val Thr Trp Gln Gln Leu Ile Asn Ile Phe
                180                 185                 190

Thr Gly Pro Ile Pro Leu Val Gln Arg Arg Pro Asp Ser Gln Cys Asn
                195                 200                 205

Ala His Asn Leu Val Tyr Arg Thr Thr Val Gly Ile Pro Val Arg Gln
        210                 215                 220

Thr Gln Phe Val Leu Tyr Val Arg Trp Gln Arg Asn Asp Pro Val Gly
225                 230                 235                 240

Glu Gly Phe Tyr Asn Cys Ala Asp Val Ile Phe Ala His Arg Leu Gly
                245                 250                 255

Ile Asn Glu Glu Asp Lys Ile Arg Pro Pro Lys Met Lys Cys Lys Gly
                260                 265                 270

Asn Asp Lys Asp Cys Tyr Lys His His His Arg His Asn Arg Tyr Glu
                275                 280                 285

Asn Asp Tyr Glu Asn Asn Tyr Glu Asn Tyr Glu Asn Tyr Glu Asn Asn
        290                 295                 300

Tyr Glu Asn Asn Tyr Glu Asn Asn Tyr Glu Asn Asn Tyr Glu Tyr Glu
305                 310                 315                 320

Tyr Glu Tyr Asp Arg Asn Asn Arg Glu His Tyr His Lys Cys Lys His
                325                 330                 335

His Ser Cys Met Gln His Asn Tyr Tyr Glu Arg Gln Tyr Asn Thr Lys
                340                 345                 350

Asp Phe Asn Tyr Val Glu Trp Asn Asp Asp Tyr Ser Asp Tyr Ile Glu
                355                 360                 365
```

```
Ile Ile Gln Asp Asn Arg Asp Met Cys Asp Ser Thr Thr Lys Cys Cys
    370                 375                 380

Tyr Lys Lys
385

<210> SEQ ID NO 12
<211> LENGTH: 245
<212> TYPE: PRT
<213> ORGANISM: Artificial Sequence
<220> FEATURE:
<223> OTHER INFORMATION: synthesized protein derived from cytoplasmic
      polyhedrosis virus

<400> SEQUENCE: 12

Met Ala Asp Val Ala Gly Thr Ser Asn Arg Asp Phe Arg Gly Arg Glu
1               5                   10                  15

Gln Arg Leu Phe Asn Ser Glu Gln Tyr Asn Tyr Asn Ser Ser Leu Asn
            20                  25                  30

Gly Glu Val Ser Val Trp Val Tyr Ala Tyr Tyr Ser Asp Gly Ser Val
        35                  40                  45

Leu Val Ile Asn Lys Asn Ser Gln Tyr Lys Val Gly Ile Ser Glu Thr
    50                  55                  60

Phe Lys Ala Leu Lys Glu Tyr Arg Glu Gly Gln His Asn Asp Ser Tyr
65                  70                  75                  80

Asp Glu Tyr Glu Val Asn Gln Ser Ile Tyr Tyr Pro Asn Gly Gly Asp
                85                  90                  95

Ala Arg Lys Phe His Ser Asn Ala Lys Pro Arg Ala Ile Gln Ile Ile
            100                 105                 110

Phe Ser Pro Ser Val Asn Val Arg Thr Ile Lys Met Ala Lys Gly Asn
            115                 120                 125

Ala Val Ser Val Pro Asp Glu Tyr Leu Gln Arg Ser His Pro Trp Glu
    130                 135                 140

Ala Thr Gly Ile Lys Tyr Arg Lys Ile Lys Arg Asp Gly Glu Ile Val
145                 150                 155                 160

Gly Tyr Ser His Tyr Phe Glu Leu Pro His Glu Tyr Asn Ser Ile Ser
                165                 170                 175

Leu Ala Val Ser Gly Val His Lys Asn Pro Ser Ser Tyr Asn Val His
            180                 185                 190

Asn Val Met Asp Val Phe Gln Ser Cys Asp Leu Ala Leu Arg Phe Cys
            195                 200                 205

Asn Arg Tyr Trp Ala Glu Leu Glu Leu Val Asn His Tyr Ile Ser Pro
    210                 215                 220

Asn Ala Tyr Pro Tyr Leu Asp Ile Asn Asn His Ser Tyr Gly Val Ala
225                 230                 235                 240

Leu Ser Asn Arg Gln
                245

<210> SEQ ID NO 13
<211> LENGTH: 245
<212> TYPE: PRT
<213> ORGANISM: Artificial Sequence
<220> FEATURE:
<223> OTHER INFORMATION: synthesized protein derived from cytoplasmic
      polyhedrosis virus

<400> SEQUENCE: 13

Met Ala Asp Val Ala Gly Thr Ser Asn Arg Asp Phe Arg Gly Arg Glu
1               5                   10                  15
```

```
Gln Arg Leu Phe Asn Ser Glu Gln Tyr Asn Tyr Asn Asn Ser Leu Asn
            20                  25                  30

Gly Glu Val Ser Val Trp Val Tyr Ala Tyr Tyr Ser Asp Gly Ser Val
            35                  40                  45

Leu Val Ile Asn Lys Asn Ser Gln Tyr Lys Val Gly Ile Ser Glu Thr
        50                  55                  60

Phe Lys Ala Leu Lys Glu Tyr Arg Glu Gly Gln His Asn Asp Ser Tyr
65                  70                  75                  80

Asp Glu Tyr Glu Val Asn Gln Ser Ile Tyr Tyr Pro Asn Gly Gly Asp
                85                  90                  95

Ala Arg Lys Phe His Ser Asn Ala Lys Pro Arg Ala Ile Gln Ile Ile
            100                 105                 110

Phe Ser Pro Ser Val Asn Val Arg Thr Ile Lys Met Ala Lys Gly Asn
            115                 120                 125

Ala Val Ser Val Pro Asp Glu Tyr Leu Gln Arg Ser His Pro Trp Glu
        130                 135                 140

Ala Thr Gly Ile Lys Tyr Arg Lys Ile Lys Arg Asp Gly Glu Ile Val
145                 150                 155                 160

Gly Tyr Ser His Tyr Phe Glu Leu Pro His Glu Tyr Asn Ser Ile Ser
                165                 170                 175

Leu Ala Val Ser Gly Val His Lys Asn Pro Ser Ser Tyr Asn Val His
            180                 185                 190

Asn Val Met Asp Val Phe Gln Ser Cys Asp Leu Ala Leu Arg Phe Cys
            195                 200                 205

Asn Arg Tyr Trp Ala Glu Leu Glu Leu Val Asn His Tyr Ile Ser Pro
        210                 215                 220

Asn Ala Tyr Pro Tyr Leu Asp Ile Asn Asn His Ser Tyr Gly Val Ala
225                 230                 235                 240

Leu Ser Asn Arg Gln
                245

<210> SEQ ID NO 14
<211> LENGTH: 30
<212> TYPE: PRT
<213> ORGANISM: Cytoplasmic polyhedrosis virus

<400> SEQUENCE: 14

Met Ala Asp Val Ala Gly Thr Ser Asn Arg Asp Phe Arg Gly Arg Glu
1               5                   10                  15

Gln Arg Leu Phe Asn Ser Glu Gln Tyr Asn Tyr Asn Asn Ser
            20                  25                  30

<210> SEQ ID NO 15
<211> LENGTH: 273
<212> TYPE: PRT
<213> ORGANISM: Artificial Sequence
<220> FEATURE:
<223> OTHER INFORMATION: synthesized protein derived from cytoplasmic
      polyhedrosis virus and aequorea victoria

<400> SEQUENCE: 15

Met Ala Asp Val Ala Gly Thr Ser Asn Arg Asp Phe Arg Gly Arg Glu
1               5                   10                  15

Gln Arg Leu Phe Asn Ser Glu Gln Tyr Asn Tyr Asn Asn Ser Gly Ser
            20                  25                  30

Ile Ala Ser Met Ser Lys Gly Glu Glu Leu Phe Thr Gly Val Val Pro
        35                  40                  45
```

-continued

```
Ile Leu Val Glu Leu Asp Gly Asp Val Asn Gly His Lys Phe Ser Val
    50              55              60

Arg Gly Glu Gly Glu Gly Asp Ala Thr Asn Gly Lys Leu Thr Leu Lys
65              70              75              80

Phe Ile Cys Thr Thr Gly Lys Leu Pro Val Pro Trp Pro Thr Leu Val
            85              90              95

Thr Thr Leu Thr Tyr Gly Val Gln Cys Phe Ser Arg Tyr Pro Asp His
            100             105             110

Met Lys Arg His Asp Phe Phe Lys Ser Ala Met Pro Glu Gly Tyr Val
        115             120             125

Gln Glu Arg Thr Ile Ser Phe Lys Asp Asp Gly Thr Tyr Lys Thr Arg
    130             135             140

Ala Glu Val Lys Phe Glu Gly Asp Thr Leu Val Asn Arg Ile Glu Leu
145             150             155             160

Lys Gly Ile Asp Phe Lys Glu Asp Gly Asn Ile Leu Gly His Lys Leu
            165             170             175

Glu Tyr Asn Phe Asn Ser His Asn Val Tyr Ile Thr Ala Asp Lys Gln
            180             185             190

Lys Asn Gly Ile Lys Ala Asn Phe Lys Ile Arg His Asn Val Glu Asp
        195             200             205

Gly Ser Val Gln Leu Ala Asp His Tyr Gln Gln Asn Thr Pro Ile Gly
    210             215             220

Asp Gly Pro Val Leu Leu Pro Asp Asn His Tyr Leu Ser Thr Gln Ser
225             230             235             240

Val Leu Ser Lys Asp Pro Asn Glu Lys Arg Asp His Met Val Leu Leu
            245             250             255

Glu Phe Val Thr Ala Ala Gly Ile Thr His Gly Met Asp Glu Leu Tyr
            260             265             270

Lys
```

```
<210> SEQ ID NO 16
<211> LENGTH: 104
<212> TYPE: PRT
<213> ORGANISM: Photorhabdus luminescens

<400> SEQUENCE: 16
```

```
Met Ile Asn Asp Met His Pro Ser Leu Ile Lys Asp Lys Asp Ile Val
1               5               10              15

Asp Asp Val Met Leu Arg Ser Cys Lys Ile Ile Ala Met Lys Val Met
            20              25              30

Pro Asp Lys Val Met Gln Val Met Val Thr Val Leu Met His Asp Gly
        35              40              45

Val Cys Glu Glu Met Leu Leu Lys Trp Asn Leu Leu Asp Asn Arg Gly
        50              55              60

Met Ala Ile Tyr Lys Val Leu Met Glu Ala Leu Cys Ala Lys Lys Asp
65              70              75              80

Val Lys Ile Ser Thr Val Gly Lys Val Gly Pro Leu Gly Cys Asp Tyr
            85              90              95

Ile Asn Cys Val Glu Ile Ser Met
            100
```

```
<210> SEQ ID NO 17
<211> LENGTH: 100
<212> TYPE: PRT
<213> ORGANISM: Photorhabdus luminescens
```

```
<400> SEQUENCE: 17

Met Ile Ile Lys Lys Asp Ile Leu Leu His Glu Asp Leu Ile Val Asp
1               5                   10                  15

Asp Glu Leu Lys Val Gly Lys Val Glu Lys Val Asn Ile Asp Ile Leu
                20                  25                  30

Ser Pro Ser Ser Val Ile Val Ser Leu Asn Ile Leu Gly Val Val Asp
            35                  40                  45

Asp Phe His Leu Leu Leu Val Asp Asp Lys Asp Lys Asp Lys Ile Val
            50                  55                  60

Leu Leu Tyr Leu Ser Leu Leu Arg Val Leu His Glu Lys Leu Asp Val
65                  70                  75                  80

Lys Val Lys Val Ala Lys Ser Asn Leu Thr Lys Met Lys Tyr Ile Val
                85                  90                  95

Gly Val Glu Ile
            100

<210> SEQ ID NO 18
<211> LENGTH: 4
<212> TYPE: PRT
<213> ORGANISM: Artificial Sequence
<220> FEATURE:
<223> OTHER INFORMATION: synthesized peptide

<400> SEQUENCE: 18

Gly Gly Gly Ser
1

<210> SEQ ID NO 19
<211> LENGTH: 328
<212> TYPE: PRT
<213> ORGANISM: Artificial Sequence
<220> FEATURE:
<223> OTHER INFORMATION: synthesyzed protein named Ubq-PhM derived from
      Homo Sapiens and Cytoplasmic polyhedrosis virus

<400> SEQUENCE: 19

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Lys Glu
            50                  55                  60

Ser Thr Leu His Leu Val Leu Arg Leu Arg Gly Gly Gly Gly Gly Ser
65                  70                  75                  80

Met Ala Asp Val Ala Gly Thr Ser Asn Arg Asp Phe Arg Gly Arg Glu
                85                  90                  95

Gln Arg Leu Phe Asn Ser Glu Gln Tyr Asn Tyr Asn Asn Ser Leu Asn
                100                 105                 110

Gly Glu Val Ser Val Trp Val Tyr Ala Tyr Tyr Ser Asp Gly Ser Val
            115                 120                 125

Leu Val Ile Asn Lys Asn Ser Gln Tyr Lys Val Gly Ile Ser Glu Thr
            130                 135                 140

Phe Lys Ala Leu Lys Glu Tyr Arg Glu Gly Gln His Asn Asp Ser Tyr
145                 150                 155                 160

Asp Glu Tyr Glu Val Asn Gln Ser Ile Tyr Tyr Pro Asn Gly Gly Asp
```

-continued

```
                   165                 170                 175

Ala Arg Lys Phe His Ser Asn Ala Lys Pro Arg Ala Ile Gln Ile Ile
            180                 185                 190

Phe Ser Pro Ser Val Asn Val Arg Thr Ile Lys Met Ala Lys Gly Asn
            195                 200                 205

Ala Val Ser Val Pro Asp Glu Tyr Leu Gln Arg Ser His Pro Trp Glu
            210                 215                 220

Ala Thr Gly Ile Lys Tyr Arg Lys Ile Lys Arg Asp Gly Glu Ile Val
225                 230                 235                 240

Gly Tyr Ser His Tyr Phe Glu Leu Pro His Glu Tyr Asn Ser Ile Ser
            245                 250                 255

Leu Ala Val Ser Gly Val His Lys Asn Pro Ser Ser Tyr Asn Val Gly
            260                 265                 270

Ser Ala His Asn Val Met Asp Val Phe Gln Ser Cys Asp Leu Ala Leu
            275                 280                 285

Arg Phe Cys Asn Arg Tyr Trp Ala Glu Leu Glu Leu Val Asn His Tyr
            290                 295                 300

Ile Ser Pro Asn Ala Tyr Pro Tyr Leu Asp Ile Asn Asn His Ser Tyr
305                 310                 315                 320

Gly Val Ala Leu Ser Asn Arg Gln
            325

<210> SEQ ID NO 20
<211> LENGTH: 328
<212> TYPE: PRT
<213> ORGANISM: Artificial Sequence
<220> FEATURE:
<223> OTHER INFORMATION: synthesyzed protein named PhM-Ubq derived from
      Homo Sapiens and Cytoplasmic polyhedrosis virus

<400> SEQUENCE: 20

Met Ala Asp Val Ala Gly Thr Ser Asn Arg Asp Phe Arg Gly Arg Glu
1               5                   10                  15

Gln Arg Leu Phe Asn Ser Glu Gln Tyr Asn Tyr Asn Asn Ser Leu Asn
            20                  25                  30

Gly Glu Val Ser Val Trp Val Tyr Ala Tyr Tyr Ser Asp Gly Ser Val
            35                  40                  45

Leu Val Ile Asn Lys Asn Ser Gln Tyr Lys Val Gly Ile Ser Glu Thr
            50                  55                  60

Phe Lys Ala Leu Lys Glu Tyr Arg Glu Gly Gln His Asn Asp Ser Tyr
65                  70                  75                  80

Asp Glu Tyr Glu Val Asn Gln Ser Ile Tyr Tyr Pro Asn Gly Gly Asp
            85                  90                  95

Ala Arg Lys Phe His Ser Asn Ala Lys Pro Arg Ala Ile Gln Ile Ile
            100                 105                 110

Phe Ser Pro Ser Val Asn Val Arg Thr Ile Lys Met Ala Lys Gly Asn
            115                 120                 125

Ala Val Ser Val Pro Asp Glu Tyr Leu Gln Arg Ser His Pro Trp Glu
            130                 135                 140

Ala Thr Gly Ile Lys Tyr Arg Lys Ile Lys Arg Asp Gly Glu Ile Val
145                 150                 155                 160

Gly Tyr Ser His Tyr Phe Glu Leu Pro His Glu Tyr Asn Ser Ile Ser
            165                 170                 175

Leu Ala Val Ser Gly Val His Lys Asn Pro Ser Ser Tyr Asn Val Gly
            180                 185                 190
```

```
Ser Ala His Asn Val Met Asp Val Phe Gln Ser Cys Asp Leu Ala Leu
        195                 200             205

Arg Phe Cys Asn Arg Tyr Trp Ala Glu Leu Glu Leu Val Asn His Tyr
    210                 215             220

Ile Ser Pro Asn Ala Tyr Pro Tyr Leu Asp Ile Asn Asn His Ser Tyr
225                 230             235                 240

Gly Val Ala Leu Ser Asn Arg Gln Gly Gly Gly Ser Met Gln Ile Phe
                245                 250             255

Val Lys Thr Leu Thr Gly Lys Thr Ile Thr Leu Glu Val Glu Pro Ser
                260             265             270

Asp Thr Ile Glu Asn Val Lys Ala Lys Ile Gln Asp Lys Glu Gly Ile
        275                 280             285

Pro Pro Asp Gln Gln Arg Leu Ile Phe Ala Gly Lys Gln Leu Glu Asp
    290                 295             300

Gly Arg Thr Leu Ser Asp Tyr Asn Ile Gln Lys Glu Ser Thr Leu His
305                 310             315                 320

Leu Val Leu Arg Leu Arg Gly Gly
                325
```

```
<210> SEQ ID NO 21
<211> LENGTH: 490
<212> TYPE: PRT
<213> ORGANISM: Artificial Sequence
<220> FEATURE:
<223> OTHER INFORMATION: synthesyzed protein named GFP-PhM derived from
      Aequorea coerulescens and Cytoplasmic polyhedrosis virus

<400> SEQUENCE: 21

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
                20                  25                  30

Gly Glu Gly Asp Ala Thr Asn Gly Lys Leu Thr Leu Lys Phe Ile Cys
            35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Thr Tyr Lys Thr Arg Ala Glu Val
                100                 105                 110

Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
        130                 135                 140

Phe Asn Ser His Asn Val Tyr Ile Thr Ala Asp Lys Gln Lys Asn Gly
145                 150                 155                 160

Ile Lys Ala Asn Phe Lys Ile Arg His Asn Val Glu Asp Gly Ser Val
                165                 170                 175

Gln Leu Ala Asp His Tyr Gln Gln Asn Thr Pro Ile Gly Asp Gly Pro
                180                 185                 190

Val Leu Leu Pro Asp Asn His Tyr Leu Ser Thr Gln Ser Val Leu Ser
                195                 200                 205

Lys Asp Pro Asn Glu Lys Arg Asp His Met Val Leu Leu Glu Phe Val
        210                 215                 220
```

Thr Ala Ala Gly Ile Thr His Gly Met Asp Glu Leu Tyr Lys Gly Gly
225                 230                 235                 240

Gly Ser Met Ala Asp Val Ala Gly Thr Ser Asn Arg Asp Phe Arg Gly
                245                 250                 255

Arg Glu Gln Arg Leu Phe Asn Ser Glu Gln Tyr Asn Tyr Asn Asn Ser
                260                 265                 270

Leu Asn Gly Glu Val Ser Val Trp Val Tyr Ala Tyr Tyr Ser Asp Gly
                275                 280                 285

Ser Val Leu Val Ile Asn Lys Asn Ser Gln Tyr Lys Val Gly Ile Ser
                290                 295                 300

Glu Thr Phe Lys Ala Leu Lys Glu Tyr Arg Glu Gly Gln His Asn Asp
305                 310                 315                 320

Ser Tyr Asp Glu Tyr Glu Val Asn Gln Ser Ile Tyr Tyr Pro Asn Gly
                325                 330                 335

Gly Asp Ala Arg Lys Phe His Ser Asn Ala Lys Pro Arg Ala Ile Gln
                340                 345                 350

Ile Ile Phe Ser Pro Ser Val Asn Val Arg Thr Ile Lys Met Ala Lys
                355                 360                 365

Gly Asn Ala Val Ser Val Pro Asp Glu Tyr Leu Gln Arg Ser His Pro
                370                 375                 380

Trp Glu Ala Thr Gly Ile Lys Tyr Arg Lys Ile Lys Arg Asp Gly Glu
385                 390                 395                 400

Ile Val Gly Tyr Ser His Tyr Phe Glu Leu Pro His Glu Tyr Asn Ser
                405                 410                 415

Ile Ser Leu Ala Val Ser Gly Val His Lys Asn Pro Ser Ser Tyr Asn
                420                 425                 430

Val Gly Ser Ala His Asn Val Met Asp Val Phe Gln Ser Cys Asp Leu
                435                 440                 445

Ala Leu Arg Phe Cys Asn Arg Tyr Trp Ala Glu Leu Glu Leu Val Asn
                450                 455                 460

His Tyr Ile Ser Pro Asn Ala Tyr Pro Tyr Leu Asp Ile Asn Asn His
465                 470                 475                 480

Ser Tyr Gly Val Ala Leu Ser Asn Arg Gln
                485                 490

<210> SEQ ID NO 22
<211> LENGTH: 361
<212> TYPE: PRT
<213> ORGANISM: Artificial Sequence
<220> FEATURE:
<223> OTHER INFORMATION: synthesyzed protein named TBD-PhM derived from
      Homo Sapiens and Cytoplasmic polyhedrosis virus

<400> SEQUENCE: 22

Thr Ser Leu Cys Cys Lys Gln Cys Gln Glu Thr Glu Ile Thr Thr Lys
1               5                   10                  15

Asn Glu Ile Phe Ser Leu Ser Leu Cys Gly Pro Met Ala Ala Tyr Val
                20                  25                  30

Asn Pro His Gly Tyr Val His Glu Thr Leu Thr Val Tyr Lys Ala Cys
        35                  40                  45

Asn Leu Asn Leu Ile Gly Arg Pro Ser Thr Glu His Ser Trp Phe Pro
    50                  55                  60

Gly Tyr Ala Trp Thr Val Ala Gln Cys Lys Ile Cys Ala Ser His Ile
65                  70                  75                  80

Gly Trp Lys Phe Thr Ala Thr Lys Lys Asp Met Ser Pro Gln Lys Phe

```
                 85                    90                    95

Trp Gly Leu Thr Arg Ser Ala Leu Leu Pro Thr Ile Pro Gly Gly Gly
             100                 105                 110

Ser Met Ala Asp Val Ala Gly Thr Ser Asn Arg Asp Phe Arg Gly Arg
             115                 120                 125

Glu Gln Arg Leu Phe Asn Ser Glu Gln Tyr Asn Tyr Asn Asn Ser Leu
         130                 135                 140

Asn Gly Glu Val Ser Val Trp Val Tyr Ala Tyr Tyr Ser Asp Gly Ser
145                 150                 155                 160

Val Leu Val Ile Asn Lys Asn Ser Gln Tyr Lys Val Gly Ile Ser Glu
                 165                 170                 175

Thr Phe Lys Ala Leu Lys Glu Tyr Arg Glu Gly Gln His Asn Asp Ser
             180                 185                 190

Tyr Asp Glu Tyr Glu Val Asn Gln Ser Ile Tyr Tyr Pro Asn Gly Gly
         195                 200                 205

Asp Ala Arg Lys Phe His Ser Asn Ala Lys Pro Arg Ala Ile Gln Ile
     210                 215                 220

Ile Phe Ser Pro Ser Val Asn Val Arg Thr Ile Lys Met Ala Lys Gly
225                 230                 235                 240

Asn Ala Val Ser Val Pro Asp Glu Tyr Leu Gln Arg Ser His Pro Trp
             245                 250                 255

Glu Ala Thr Gly Ile Lys Tyr Arg Lys Ile Lys Arg Asp Gly Glu Ile
             260                 265                 270

Val Gly Tyr Ser His Tyr Phe Glu Leu Pro His Glu Tyr Asn Ser Ile
         275                 280                 285

Ser Leu Ala Val Ser Gly Val His Lys Asn Pro Ser Ser Tyr Asn Val
     290                 295                 300

Gly Ser Ala His Asn Val Met Asp Val Phe Gln Ser Cys Asp Leu Ala
305                 310                 315                 320

Leu Arg Phe Cys Asn Arg Tyr Trp Ala Glu Leu Glu Leu Val Asn His
             325                 330                 335

Tyr Ile Ser Pro Asn Ala Tyr Pro Tyr Leu Asp Ile Asn Asn His Ser
             340                 345                 350

Tyr Gly Val Ala Leu Ser Asn Arg Gln
         355                 360
```

<210> SEQ ID NO 23
<211> LENGTH: 361
<212> TYPE: PRT
<213> ORGANISM: Artificial Sequence
<220> FEATURE:
<223> OTHER INFORMATION: synthesyzed protein named PhM-TBD derived from
      Homo Sapiens and Cytoplasmic polyhedrosis virus

<400> SEQUENCE: 23

```
Met Ala Asp Val Ala Gly Thr Ser Asn Arg Asp Phe Arg Gly Arg Glu
1               5                   10                  15

Gln Arg Leu Phe Asn Ser Glu Gln Tyr Asn Tyr Asn Asn Ser Leu Asn
             20                  25                  30

Gly Glu Val Ser Val Trp Val Tyr Ala Tyr Tyr Ser Asp Gly Ser Val
         35                  40                  45

Leu Val Ile Asn Lys Asn Ser Gln Tyr Lys Val Gly Ile Ser Glu Thr
     50                  55                  60

Phe Lys Ala Leu Lys Glu Tyr Arg Glu Gly Gln His Asn Asp Ser Tyr
65                  70                  75                  80
```

-continued

```
Asp Glu Tyr Glu Val Asn Gln Ser Ile Tyr Tyr Pro Asn Gly Gly Asp
            85                  90                  95

Ala Arg Lys Phe His Ser Asn Ala Lys Pro Arg Ala Ile Gln Ile Ile
            100                 105                 110

Phe Ser Pro Ser Val Asn Val Arg Thr Ile Lys Met Ala Lys Gly Asn
            115                 120                 125

Ala Val Ser Val Pro Asp Glu Tyr Leu Gln Arg Ser His Pro Trp Glu
    130                 135                 140

Ala Thr Gly Ile Lys Tyr Arg Lys Ile Lys Arg Asp Gly Glu Ile Val
145                 150                 155                 160

Gly Tyr Ser His Tyr Phe Glu Leu Pro His Glu Tyr Asn Ser Ile Ser
                165                 170                 175

Leu Ala Val Ser Gly Val His Lys Asn Pro Ser Ser Tyr Asn Val Gly
                180                 185                 190

Ser Ala His Asn Val Met Asp Val Phe Gln Ser Cys Asp Leu Ala Leu
            195                 200                 205

Arg Phe Cys Asn Arg Tyr Trp Ala Glu Leu Glu Leu Val Asn His Tyr
    210                 215                 220

Ile Ser Pro Asn Ala Tyr Pro Tyr Leu Asp Ile Asn Asn His Ser Tyr
225                 230                 235                 240

Gly Val Ala Leu Ser Asn Arg Gln Gly Gly Gly Ser Thr Ser Leu Cys
                245                 250                 255

Cys Lys Gln Cys Gln Glu Thr Glu Ile Thr Thr Lys Asn Glu Ile Phe
                260                 265                 270

Ser Leu Ser Leu Cys Gly Pro Met Ala Ala Tyr Val Asn Pro His Gly
            275                 280                 285

Tyr Val His Glu Thr Leu Thr Val Tyr Lys Ala Cys Asn Leu Asn Leu
    290                 295                 300

Ile Gly Arg Pro Ser Thr Glu His Ser Trp Phe Pro Gly Tyr Ala Trp
305                 310                 315                 320

Thr Val Ala Gln Cys Lys Ile Cys Ala Ser His Ile Gly Trp Lys Phe
                325                 330                 335

Thr Ala Thr Lys Lys Asp Met Ser Pro Gln Lys Phe Trp Gly Leu Thr
            340                 345                 350

Arg Ser Ala Leu Leu Pro Thr Ile Pro
            355                 360
```

```
<210> SEQ ID NO 24
<211> LENGTH: 114
<212> TYPE: PRT
<213> ORGANISM: Cytoplasmic polyhedrosis virus

<400> SEQUENCE: 24
```

```
Met Ala Asp Val Ala Gly Thr Ser Asn Arg Asp Phe Arg Gly Arg Glu
1               5                   10                  15

Gln Arg Leu Phe Asn Ser Glu Gln Tyr Asn Tyr Asn Asn Ser Leu Asn
            20                  25                  30

Gly Glu Val Ser Val Trp Val Tyr Ala Tyr Tyr Ser Asp Gly Ser Val
            35                  40                  45

Leu Val Ile Asn Lys Asn Ser Gln Tyr Lys Val Gly Ile Ser Glu Thr
    50                  55                  60

Phe Lys Ala Leu Lys Glu Tyr Arg Glu Gly Gln His Asn Asp Ser Tyr
65                  70                  75                  80

Asp Glu Tyr Glu Val Asn Gln Ser Ile Tyr Tyr Pro Asn Gly Gly Asp
                85                  90                  95
```

```
Ala Arg Lys Phe His Ser Asn Ala Lys Pro Arg Ala Ile Gln Ile Ile
            100                 105                 110

Phe Ser

<210> SEQ ID NO 25
<211> LENGTH: 155
<212> TYPE: PRT
<213> ORGANISM: Cytoplasmic polyhedrosis virus

<400> SEQUENCE: 25

Met Ala Asp Val Ala Gly Thr Ser Asn Arg Asp Phe Arg Gly Arg Glu
1               5                   10                  15

Gln Arg Leu Phe Asn Ser Glu Gln Tyr Asn Tyr Asn Asn Ser Leu Asn
            20                  25                  30

Gly Glu Val Ser Val Trp Val Tyr Ala Tyr Tyr Ser Asp Gly Ser Val
            35                  40                  45

Leu Val Ile Asn Lys Asn Ser Gln Tyr Lys Val Gly Ile Ser Glu Thr
        50                  55                  60

Phe Lys Ala Leu Lys Glu Tyr Arg Glu Gly Gln His Asn Asp Ser Tyr
65                  70                  75                  80

Asp Glu Tyr Glu Val Asn Gln Ser Ile Tyr Tyr Pro Asn Gly Gly Asp
                85                  90                  95

Ala Arg Lys Phe His Ser Asn Ala Lys Pro Arg Ala Ile Gln Ile Ile
            100                 105                 110

Phe Ser Pro Ser Val Asn Val Arg Thr Ile Lys Met Ala Lys Gly Asn
            115                 120                 125

Ala Val Ser Val Pro Asp Glu Tyr Leu Gln Arg Ser His Pro Trp Glu
        130                 135                 140

Ala Thr Gly Ile Lys Tyr Arg Lys Ile Lys Arg
145                 150                 155

<210> SEQ ID NO 26
<211> LENGTH: 133
<212> TYPE: PRT
<213> ORGANISM: Cytoplasmic polyhedrosis virus

<400> SEQUENCE: 26

Ser Val Asn Val Arg Thr Ile Lys Met Ala Lys Gly Asn Ala Val Ser
1               5                   10                  15

Val Pro Asp Glu Tyr Leu Gln Arg Ser His Pro Trp Glu Ala Thr Gly
            20                  25                  30

Ile Lys Tyr Arg Lys Ile Lys Arg Asp Gly Glu Ile Val Gly Tyr Ser
            35                  40                  45

His Tyr Phe Glu Leu Pro His Glu Tyr Asn Ser Ile Ser Leu Ala Val
        50                  55                  60

Ser Gly Val His Lys Asn Pro Ser Ser Tyr Asn Val Gly Ser Ala His
65                  70                  75                  80

Asn Val Met Asp Val Phe Gln Ser Cys Asp Leu Ala Leu Arg Phe Cys
                85                  90                  95

Asn Arg Tyr Trp Ala Glu Leu Glu Leu Val Asn His Tyr Ile Ser Pro
            100                 105                 110

Asn Ala Tyr Pro Tyr Leu Asp Ile Asn Asn His Ser Tyr Gly Val Ala
            115                 120                 125

Leu Ser Asn Arg Gln
        130
```

-continued

```
<210> SEQ ID NO 27
<211> LENGTH: 191
<212> TYPE: PRT
<213> ORGANISM: Cytoplasmic polyhedrosis virus

<400> SEQUENCE: 27

Lys Val Gly Ile Ser Glu Thr Phe Lys Ala Leu Lys Glu Tyr Arg Glu
1               5                   10                  15

Gly Gln His Asn Asp Ser Tyr Asp Glu Tyr Glu Val Asn Gln Ser Ile
            20                  25                  30

Tyr Tyr Pro Asn Gly Gly Asp Ala Arg Lys Phe His Ser Asn Ala Lys
        35                  40                  45

Pro Arg Ala Ile Gln Ile Ile Phe Ser Pro Ser Val Asn Val Arg Thr
    50                  55                  60

Ile Lys Met Ala Lys Gly Asn Ala Val Ser Val Pro Asp Glu Tyr Leu
65                  70                  75                  80

Gln Arg Ser His Pro Trp Glu Ala Thr Gly Ile Lys Tyr Arg Lys Ile
            85                  90                  95

Lys Arg Asp Gly Glu Ile Val Gly Tyr Ser His Tyr Phe Glu Leu Pro
            100                 105                 110

His Glu Tyr Asn Ser Ile Ser Leu Ala Val Ser Gly Val His Lys Asn
        115                 120                 125

Pro Ser Ser Tyr Asn Val Gly Ser Ala His Asn Val Met Asp Val Phe
    130                 135                 140

Gln Ser Cys Asp Leu Ala Leu Arg Phe Cys Asn Arg Tyr Trp Ala Glu
145                 150                 155                 160

Leu Glu Leu Val Asn His Tyr Ile Ser Pro Asn Ala Tyr Pro Tyr Leu
                165                 170                 175

Asp Ile Asn Asn His Ser Tyr Gly Val Ala Leu Ser Asn Arg Gln
            180                 185                 190
```

PROTEIN CRYSTAL PRODUCTION METHOD AND CRYSTALLINE STRUCTURE ANALYSIS METHOD

FIELD OF INVENTION

The present invention relates to a production method for a protein crystal and a crystal structure analysis method. Priority is claimed on Japanese Patent Application No. 2020-027386, filed Feb. 20, 2020, the content of which is incorporated herein by reference.

DESCRIPTION OF RELATED ART

A structural analysis of proteins is important for the determination of three-dimensional structures of proteins and studies on the structural and functional correlations. In order to carry out a structural analysis of proteins, it is necessary to produce high-quality protein crystals. The quality of protein crystals has tremendous influence on the accuracy and reliability of protein crystal structure analysis. For this reason, crystallization of a protein is the largest rate-determining step in a structural analysis of the protein.

Crystallization of a protein involves many factors such as the concentration of the protein, purity, the type of a buffer solution, pH, the type and concentration of a precipitant, temperature, an organic solvent, metal ions, and the type and concentration of a surfactant. Therefore, in order to produce a high-quality protein crystal and perform a crystal structure analysis, it is necessary to consider numerous conditions, and a great deal of effort is needed (see, for example, Non-Patent Document 1).

However, on the surface of protein molecules, there are amino acid side chains having various functional groups with functionality, and the functional groups have unique chemical properties. Further, there are cases where a plurality of protein molecules are regularly arranged to form a cage-like three-dimensional structure (protein cage).

For example, polyhedrosis viruses are viruses that infect cells of insects such as silkworms. Polyhedrosis viruses produce, in the late stage of infection, inclusion bodies called polyhedra in infected cells in a large quantity that reach about half the total quantity of cellular proteins, and enclose a large number of virus particles in the inclusion bodies. Polyhedrin, which is a polyhedral protein, is an example of the above-mentioned protein that forms a protein cage.

Regarding the protein that forms a protein cage, DNA binding proteins from starved cells (DPS), capsids of viruses containing RNA, and the like are also known in addition to polyhedrin protein. Protein cages formed from these proteins may be regularly arranged to form crystals.

For example, Patent Document 1 describes that a modified polyhedrin having at least a portion of the amino acid sequence deleted has a polyhedron-forming ability. Furthermore, it describes that a crystal structure analysis could be performed by using a polyhedron formed from this modified polyhedrin protein.

CITATION LIST

Patent Document

[Patent Document 1]
Japanese Unexamined Patent Application, First Publication No. 2018-033404

Non-Patent Document

[Non-Patent Document 1]
ASHIDA, Tamaichi, Let's Begin X-ray Structure Analysis: (9) Introduction to Protein Crystal Structure Analysis, Journal of the Crystallographic Society of Japan, 38, 378-388, 1996.

SUMMARY OF INVENTION

Technical Problem

An object of the present invention is to provide a technology for conveniently producing a crystal of a protein.

Solution to Problem

The present invention includes the following embodiments.

[1] A production method for a crystal of a crystalline protein, the method including:
a step of inducing expression of a crystalline protein in *Escherichia coli* into which an expression construct of the crystalline protein has been introduced, and incubating the *Escherichia coli* for a predetermined time until a crystal of the crystalline protein is formed inside the *Escherichia coli*.

[2] The production method according to [1],
in which the *Escherichia coli* further has an expression construct of a non-crystalline protein introduced therein,
in the step of incubating, the non-crystalline protein is induced to be expressed together with the crystalline protein, and
the crystal formed inside the *Escherichia coli* is a co-crystal of the crystalline protein and the non-crystalline protein.

[3] The production method according to [1] or [2],
in which the crystalline protein is a protein described in any one of the following items (i) to (iii):
(i) a cytoplasmic polyhedral protein, a nuclear polyhedral protein, cathepsin B, ferritin, DNA-binding proteins from starved cells (DPS), luciferase, reovirus nonstructural protein (μNS), fusolin protein (Fusolin), Crystalline inclusion protein A (CipA) or Crystalline inclusion protein B (CipB);
(ii) a protein having an amino acid sequence in which one amino acid or a plurality of amino acids have been deleted, substituted, or added in an amino acid sequence of the protein of (i) and having a crystal-forming ability; and
(iii) a fusion protein of the protein of (i) or (ii) and a target peptide.

[4] The production method according to any one of [1] to [3], in which the crystalline protein is a fusion protein having a target peptide inserted between the 66th amino acid and the 67th amino acid of an amino acid sequence set forth in SEQ ID NO:1, or between an amino acid corresponding to the 66th amino acid of the amino acid sequence set forth in SEQ ID NO:1 and an amino acid corresponding to the 67th amino acid thereof in an amino acid sequence of a protein including an amino acid sequence in which one amino acid or a plurality of amino acids have been deleted, substituted, or added in the amino acid sequence set forth in SEQ ID NO:1 and having a crystal-forming ability.

[5] The production method according to any one of [1] to [4], in which the predetermined time is 3 to 30 hours.

[6] The production method according to any one of [1] to [5], in which the step of incubating is carried out at 18° C. to 40° C.

[7] A crystal structure analysis method, including:

a step of subjecting a crystal produced by the production method according to any one of [1] to [6] to an X-ray crystal structure analysis together with the *Escherichia coli*.

Advantageous Effects of Invention

According to the present invention, a technology for conveniently producing a crystal of a protein can be provided.

BRIEF DESCRIPTION OF DRAWINGS

FIG. 13A right part is a photograph showing the result of observing the crystals of the fusion proteins with a scanning electron microscope in Experimental Example 7.

FIG. 13B right part is a photograph showing the result of observing the crystals of the fusion proteins with a scanning electron microscope in Experimental Example 7.

FIG. 15B lower part is a photograph showing the result of observing the crystals of the fusion proteins with a scanning electron microscope in Experimental Example 10.

FIG. 15C lower part is a photograph showing the result of observing the crystals of the fusion proteins with a scanning electron microscope in Experimental Example 10.

FIG. 16B is a graph showing the result of performing a MALDI-TOF MS analysis of the collected crystals of the fragments of the cytoplasmic polyhedral proteins in Experimental Example 11.

FIG. 16C is a photograph showing the result of observing crystals of fragments of cytoplasmic polyhedral proteins with a scanning electron microscope in Experimental Example 11.

FIG. 16D is a graph showing the result of performing a MALDI-TOF MS analysis of the collected crystals of the fragments of the cytoplasmic polyhedral proteins in Experimental Example 11.

DETAILED DESCRIPTION OF THE INVENTION

[Production Method for Protein Crystal]

Figure 1B:
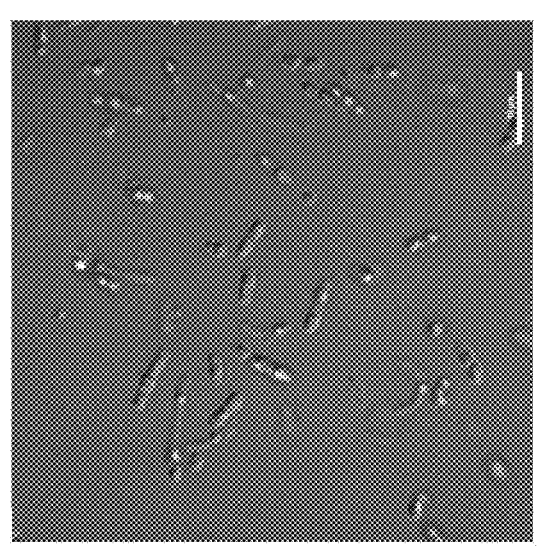
FIG. 1B is an optical microphotograph of *Escherichia coli* in which crystals (polyhedra) of CPV-derived polyhedrin were formed inside the bacterial cells in Experimental Example 1.

According to an embodiment, the present invention provides a production method for a crystal of a crystalline protein, the method including a step of inducing expression of a crystalline protein in *Escherichia coli* into which an expression construct of the crystalline protein has been introduced, and incubating the *Escherichia coli* for a predetermined time until a crystal of the crystalline protein is formed inside the *Escherichia coli*.

The crystalline protein is not particularly limited as long as it is a protein that forms a crystal in *Escherichia coli*.

Even for a non-crystalline protein that originally does not form a crystal, when the non-crystalline protein becomes capable of forming a crystal in *Escherichia coli* by means of techniques such as chemical modification of the protein, creation of a variant, and a fusion protein, this protein is also included in the crystalline protein according to the present specification.

More limited examples of the crystalline protein include the proteins described in any of the following (i) to (iii):

(i) a cytoplasmic polyhedral protein, a nuclear polyhedral protein, cathepsin B, ferritin, DPS, luciferase, μNS, Fusolin, CipA, or CipB;

(ii) a protein consisting of an amino acid sequence in which one amino acid or a plurality of amino acids have been deleted, substituted, or added in an amino acid sequence of the protein of (i) and having a crystal-forming ability; and (iii) a fusion protein of the protein of (i) or (ii) and a target peptide.

The nuclear polyhedral protein is a polyhedrin protein derived from a nuclear polyhedrosis virus (Nucleopolyhedrovirus, NPV), which is a pathogenic virus for nuclear polyhedrosis. The cytoplasmic polyhedral protein is a polyhedrin protein derived from a cytoplasmic polyhedrosis virus (Cypovirus, CPV), which is a pathogenic virus for cytoplasmic polyhedrosis. An amino acid sequence of the cytoplasmic polyhedral protein is set forth in SEQ ID NO:2, and an amino acid sequence of the nuclear polyhedral protein is set forth in SEQ ID NO:3.

Cathepsin B is a protease having endopeptidase activity and exopeptidase activity. Cathepsin B is a protein that forms a crystal in cultured insect cells. An amino acid sequence of *Trypanosoma brucei*-derived cathepsin B is set forth in SEQ ID NO:4.

Ferritin is a protein synthesized by almost all living organisms including algae, bacteria, plants, humans, and non-human animals. Ferritin forms a cage consisting of 24-mers and is responsible for in vivo iron storage by including iron ions. The outer diameter is about 12 nm.

Ferritin is not particularly limited, and examples thereof include horse-derived ferritin and human-derived ferritin. An amino acid sequence of horse-derived ferritin L chain is set forth in SEQ ID NO:5, and an amino acid sequence of human-derived ferritin L chain is set forth in SEQ ID NO:6.

DPS is a protein belonging to the ferritin superfamily, which is synthesized by many bacteria. DPS forms a cage consisting of 12-mers and protects chromosomal DNA from oxidative stress and the like by including the chromosomal DNA. The outer diameter is about 9 nm. The amino acid sequence of *Escherichia coli*-derived DPS is set forth in SEQ ID NO:7.

Luciferase is a generic name for enzymes that have the action of catalyzing a chemical reaction in which a luminescent material emits light in bioluminescence of luminescent bacteria, fireflies, and the like. Luciferase is a protein that forms a crystal in insect cells. An amino acid sequence of firefly-derived luciferase is set forth in SEQ ID NO: 8, and an amino acid sequence of sea pansy-derived luciferase is set forth in SEQ ID NO:9.

μNS is reovirus nonstructural protein having crystallinity. An amino acid sequence of reovirus-derived μNS is set forth in SEQ ID NO:10.

Fusolin is a constituent protein of a crystalline protein inclusion body formed in host cells by Entomopoxvirus. An amino acid sequence of Entomopoxvirus-derived Fusolin is set forth in SEQ ID NO:11.

CipA and CipB are constituent proteins of a crystalline protein inclusion body formed in the cytoplasm by *Photorhabdus luminescens*, which is an insect pathogenic bacterium. An amino acid sequence of CipA is set forth in SEQ ID NO:16, and an amino acid sequence of CipB is set forth in SEQ ID NO:17.

The crystalline protein may be a variant having a mutation in the above-mentioned cytoplasmic polyhedral protein, nuclear polyhedral protein, cathepsin B, ferritin, DPS, luciferase, μNS, Fusolin, CipA, CipB, and the like as long as it has a crystal-forming ability. More specifically, the crystalline protein may be, for example, a protein including an amino acid sequence in which one amino acid or a plurality of amino acids have been deleted, substituted, or added in any of the above-mentioned amino acid sequences set forth in SEQ ID NO:2 to SEQ ID NO:11, SEQ ID NO:16, and SEQ ID NO:17.

Here, one amino acid or a plurality of amino acids may be, for example, 1 to 50 amino acids, may be 1 to 40 amino acids for example, may be 1 to 30 amino acids for example, may be 1 to 20 amino acids for example, may be 1 to 10 amino acids for example, may be 1 to 5 amino acids for example, or may be 1 to 3 amino acids for example. As will be described later in the Examples, the inventors have confirmed that even when 38 amino acids of the polyhedrin protein are deleted, the polyhedrin protein has a crystal-forming ability.

Furthermore, the crystalline protein may also be the above-mentioned fusion protein of a protein and a target peptide as long as it has the crystal-forming ability. That is, the crystalline protein may also be a fusion protein of the above-mentioned cytoplasmic polyhedral protein, nuclear polyhedral protein, cathepsin B, ferritin, DPS, luciferase, μNS, Fusolin, CipA, CipB, or a variant of any of these crystalline proteins, and a target peptide.

Here, the target peptide may be, for example, a peptide as an object whose three-dimensional structure is to be analyzed. As will be described later, the three-dimensional structure of a target peptide can be conveniently analyzed by causing a crystalline protein, which is a fusion protein of the above-mentioned crystalline protein and a target peptide, to be expressed in *Escherichia coli* to form a crystal, and subjecting the crystal of the crystalline protein to an X-ray crystal structure analysis together with the *Escherichia coli*.

In this case, the target peptide may be any peptide in need of analysis of the three-dimensional structure. The amino acid length of the target peptide is preferably, for example, about 5 to 50 amino acids from the viewpoint that the crystalline protein can maintain the crystal-forming ability.

With regard to the fusion protein of a variant of a crystalline protein and a target peptide, the crystalline protein may be the amino acid sequence set forth in SEQ ID NO:1, and the fusion protein may be a fusion protein having the target peptide inserted between the 66th amino acid and the 67th amino acid of the amino acid sequence set forth in SEQ ID NO:1.

Alternatively, with regard to the fusion protein of a variant of a crystalline protein and a target peptide, the crystalline protein may be a mutant protein having the amino acid sequence set forth in SEQ ID NO:1. More specifically, the mutant protein having the amino acid sequence set forth in SEQ ID NO:1 may be a protein including an amino acid sequence in which one amino acid or a plurality of amino acids have been deleted, substituted, or added in the amino acid sequence set forth in SEQ ID NO:1 and having a crystal-forming ability. Here, the phrase one amino acid or a plurality of amino acids is the same as that described above.

Further, the fusion protein may also be a fusion protein having a target peptide inserted between the amino acid corresponding to the 66th amino acid and the amino acid corresponding to the 67th amino acid of the amino acid sequence set forth in SEQ ID NO:1, in a mutant protein of the protein including the amino acid sequence set forth in SEQ ID NO:1.

The amino acid corresponding to the 66th amino acid and the amino acid corresponding to the 67th amino acid of the amino acid sequence set forth in SEQ ID NO:1 can be identified by aligning the amino acid sequence set forth in SEQ ID NO:1 with the amino acid sequence of the mutant protein by using, for example, software such as ClustalW.

With regard to the production method of the present embodiment, the *Escherichia coli* further has an expression construct of a non-crystalline protein introduced therein, and in the step of incubating, the non-crystalline protein may be induced to be expressed together with the crystalline protein, while the crystal formed inside the *Escherichia coli* may be a co-crystal of the crystalline protein and the non-crystalline protein.

According to the present specification, the term non-crystalline protein usually means a protein that does not form a crystal in *Escherichia coli*. Regarding the non-crystalline protein, any protein having a molecular weight of about 1,000 to 100,000 can be used without particular limitation.

For example, a co-crystal may also be produced by using an unstable protein such as a membrane protein to produce a co-crystal as the non-crystalline protein. As a result, an unstable protein such as a membrane protein can be easily purified as a co-crystal. Furthermore, an unstable protein such as a membrane protein can be stably stored in the form of a co-crystal.

Regarding the non-crystalline protein, one kind thereof may be used alone, or two or more kinds thereof may be used as a mixture. Furthermore, when two or more kinds of the non-crystalline proteins are used, those non-crystalline proteins may form a complex.

Furthermore, the non-crystalline protein may be a fusion protein with a portion of the crystalline protein. As a result, there is a tendency that the non-crystalline protein is easily incorporated into the crystal of the crystalline protein, and a co-crystal is easily formed.

The expression method for the above-mentioned crystalline protein and non-crystalline protein in *Escherichia coli* is not particularly limited, and the proteins may be expressed by methods that are conventionally carried out. For example, the expression of a crystalline protein or a non-crystalline protein may be induced by incubating *Escherichia coli* into which an expression construct of the crystalline protein or the non-crystalline protein has been introduced, in a medium.

The introduction of an expression construct into *Escherichia coli* may be carried out by, for example, introducing an expression vector of a crystalline protein or a non-crystalline protein in the form of a plasmid or the like into *Escherichia coli*, or may be carried out by inserting an expression construct of the crystalline protein or the non-crystalline protein into the genome of *Escherichia coli*.

Furthermore, induction of the expression of the crystalline protein or the non-crystalline protein can be carried out by an appropriate method according to the characteristics of the expression construct of the crystalline protein or the non-crystalline protein. For example, induction of the expression of the crystalline protein or the non-crystalline protein may also be carried out by utilizing an expression control system that utilizes a lactose operon and adding isopropyl β-D-thiogalactopyranoside (IPTG) to the medium.

Alternatively, induction of the expression of the crystalline protein or the non-crystalline protein may also be carried out by utilizing an expression control system based on the Tet-on/Tet-off system and adding tetracycline or a derivative thereof into the medium or removing tetracycline or a derivative thereof from the medium.

Alternatively, an embodiment in which the expression of the crystalline protein or the non-crystalline protein is initiated at the same time as the initiation of the culture of *Escherichia coli* without implementing the expression induction control, may also be adopted.

In the production method of the present embodiment, the expression of the crystalline protein or the non-crystalline protein is induced in *Escherichia coli* into which an expression construct of the crystalline protein or the non-crystalline protein has been introduced. It is preferable that the expression induction be carried out, for example, after the $OD_{600}$ of *Escherichia coli* reaches 0.6 to 0.8.

Culturing of *Escherichia coli* may be carried out in a small amount of medium of about 10 mL. As will be described later in the Examples, the inventors clarified that a large quantity of crystals of a protein can be produced even with such a small amount of medium, and that a structural analysis of the protein can be carried out by subjecting the crystals to X-ray crystal structure analysis together with *Escherichia coli*.

Subsequently, after inducing the expression of the crystalline protein or the non-crystalline protein, the *Escherichia coli* is incubated for a predetermined time until a crystal of the crystalline protein or a co-crystal of the crystalline protein and the non-crystalline protein is formed inside the *Escherichia coli*. Here, the predetermined time may be 3 to 30 hours and may be, for example, 3 to 24 hours. As will be described later in the Examples, the inventors have clarified that a structural analysis of a protein can be performed by incubating the *Escherichia coli* for merely 20 to 24 hours to form crystals and then performing X-ray crystal structure analysis together with *Escherichia coli*.

Furthermore, the temperature at the time of incubating until a crystal of the crystalline protein or a co-crystal of the crystalline protein and the non-crystalline protein is formed may be 18° C. to 40° C., may be 25° C. to 38° C., or may be about 30° C. When the temperature at the time of incubating until a crystal of the crystalline protein or a co-crystal of the crystalline protein and the non-crystalline protein is formed is in the above-described range, the quality of the formed protein crystals tends to be enhanced.

[Crystal Structure Analysis Method]

According to an embodiment, the present invention provides a crystal structure analysis method including a step of subjecting a crystal produced by the above-mentioned production method to an X-ray crystal structure analysis together with the *Escherichia coli*.

As will be described later in the Examples, the inventors clarified that, surprisingly, a structural analysis of a protein can be performed by subjecting *Escherichia coli* that has formed protein crystals inside the bacterial cells to X-ray crystal structure analysis together with *Escherichia coli*. That is, it is possible to perform X-ray crystal structure analysis together with *Escherichia coli* without purifying the protein crystals. According to the method of the present embodiment, a structural analysis of a protein can be performed remarkably conveniently as compared with the related art technologies.

EXAMPLES

Hereinafter, the present invention will be described by way of Examples; however, the present invention is not intended to be limited to the following Examples.

Experimental Example 1

(Crystallization of Protein in *Escherichia coli* 1)

A gene encoding CPV-derived polyhedrin (the amino acid sequence is set forth in SEQ ID NO:2) and a gene encoding NPV-derived polyhedrin (the amino acid sequence is set forth in SEQ ID NO:3) were each inserted into a pET29b vector (Merck Millipore Corporation), and expression vectors were produced. Subsequently, each of the expression vectors was used to transform *Escherichia coli* strain BL21.

Subsequently, each group of the transformed *Escherichia coli* was inoculated into 10 mL of LB medium and was cultured at 37° C. until the $OD_{600}$ reached 0.6 to 0.8. Subsequently, IPTG was added thereto so as to obtain a final concentration of 0.5 mM, and expression of the polyhedrin was induced. Subsequently, the cells were cultured at 30° C. for 20 to 24 hours, and polyhedrin crystals were formed.

Figure 1A:
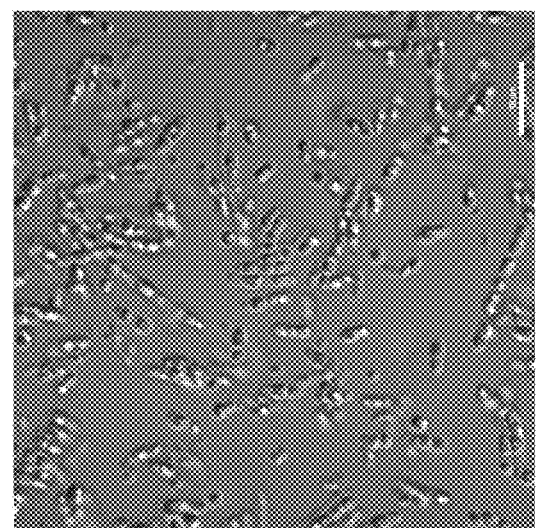
FIG. 1A is an optical microphotograph of *Escherichia coli* in which crystals (polyhedra) of CPV-derived polyhedrin were formed inside the bacterial cells in Experimental Example 1.
Figure 1D:
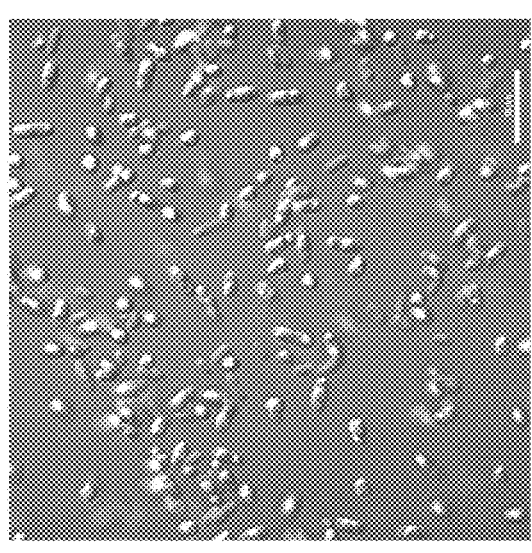
FIG. 1D is an optical microphotograph of *Escherichia coli* in which crystals of NPV-derived polyhedrin were formed inside the bacterial cells in Experimental Example 1.
Figure 1C:
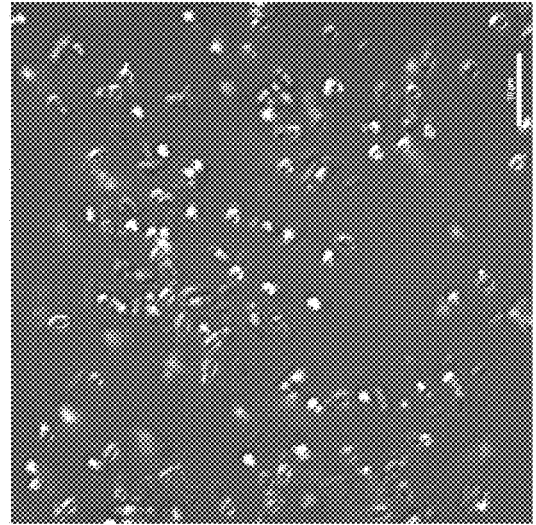
FIG. 1C is an optical microphotograph of *Escherichia coli* in which crystals of NPV-derived polyhedrin were formed inside the bacterial cells in Experimental Example 1.

FIGS. 1A and 1B are optical microphotographs of *Escherichia coli* in which crystals of (polyhedra) of CPV-derived polyhedrin were formed inside the bacterial cells. Furthermore, FIGS. 1C and 1D are optical microphotographs of *Escherichia coli* in which crystals of NPV-derived polyhedrin were formed inside the bacterial cells. In FIGS. 1A to 1D, the scale bar indicates 10 μm.

Figure 2A:
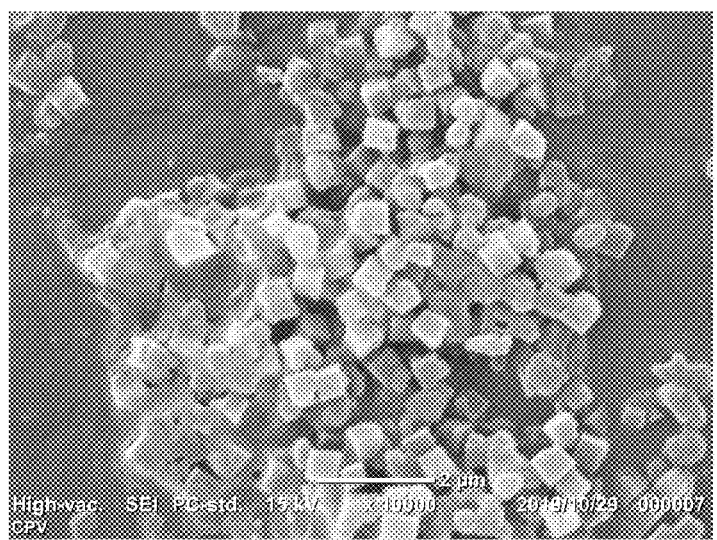
FIG. 2A is a photograph showing the result of observing the crystals of CPV-derived polyhedrin with a scanning electron microscope in Experimental Example 1.
Figure 2B:
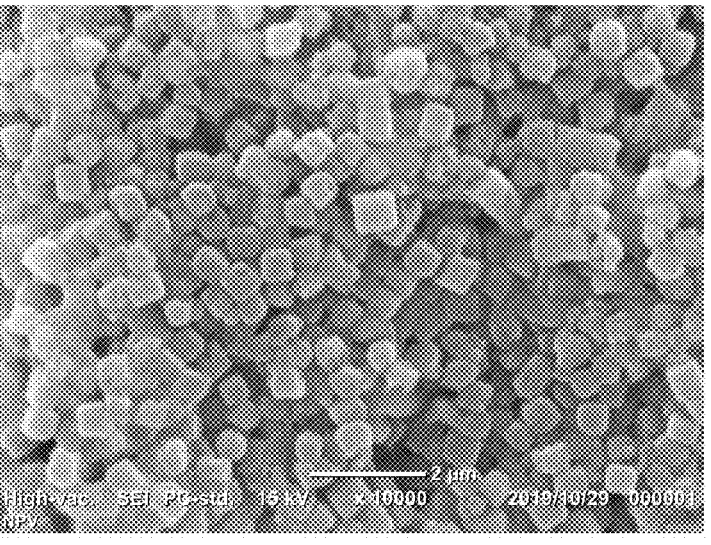
FIG. 2B is a photograph showing the result of observing the crystals of NPV-derived polyhedrin with a scanning electron microscope in Experimental Example 1.

Subsequently, each group of *Escherichia coli* was collected by centrifugation. Subsequently, *Escherichia coli* was ultrasonically crushed, and crystals of polyhedrin were collected by centrifugation. FIG. 2A is a photograph showing the results of observing the crystals of CPV-derived polyhedrin with a scanning electron microscope. FIG. 2B is a photograph showing the results of observing the crystals of NPV-derived polyhedrin with a scanning electron microscope. In FIGS. 2A and 2B, the scale bar indicates 2 μm. As a result, cubic crystals were observed in all the samples, and it was confirmed that polyhedral crystals can be formed in *Escherichia coli*.

Figure 3:
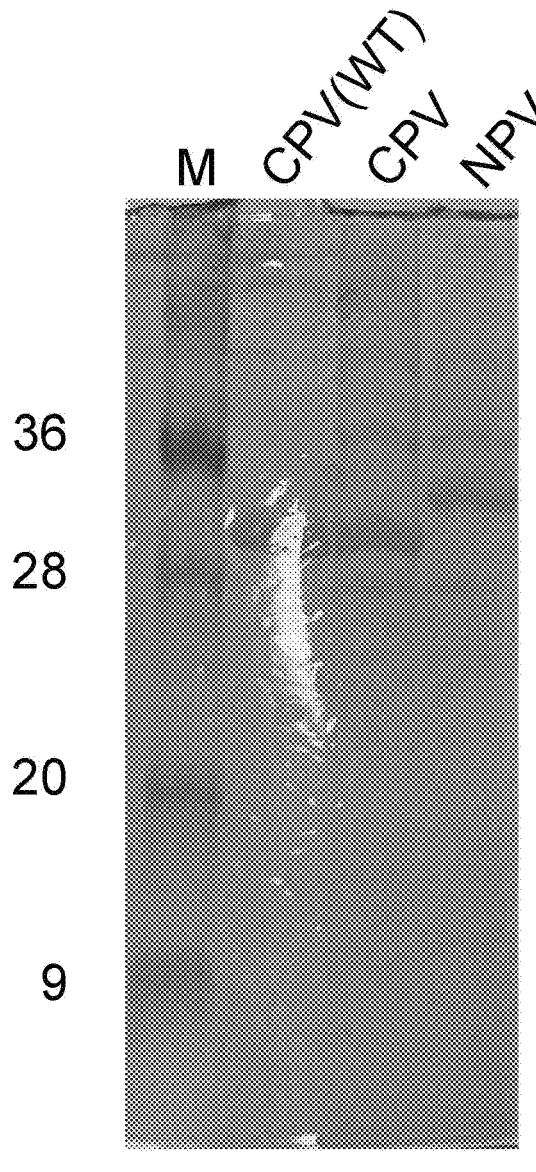
FIG. 3 is a photograph showing the result of SDS-polyacrylamide gel electrophoresis (PAGE) in Experimental Example 1.

FIG. 3 is a photograph showing the results obtained by submitting the collected crystals of CPV-derived polyhedrin and the collected crystals of NPV-derived polyhedrin to SDS-polyacrylamide gel electrophoresis (PAGE) and performing Coomassie Brilliant Blue staining. In FIG. 3, "M" denotes a molecular weight marker, and "CPV (WT)" denotes a crystal of CPV-derived polyhedrin expressed in the insect cell strain Sf21, which was submitted to SDS-PAGE as a control.

As a result, it was confirmed that both the CPV-derived polyhedrin and the NPV-derived polyhedrin expressed in *Escherichia coli* have the predicted molecular weights.

Figure 4A:
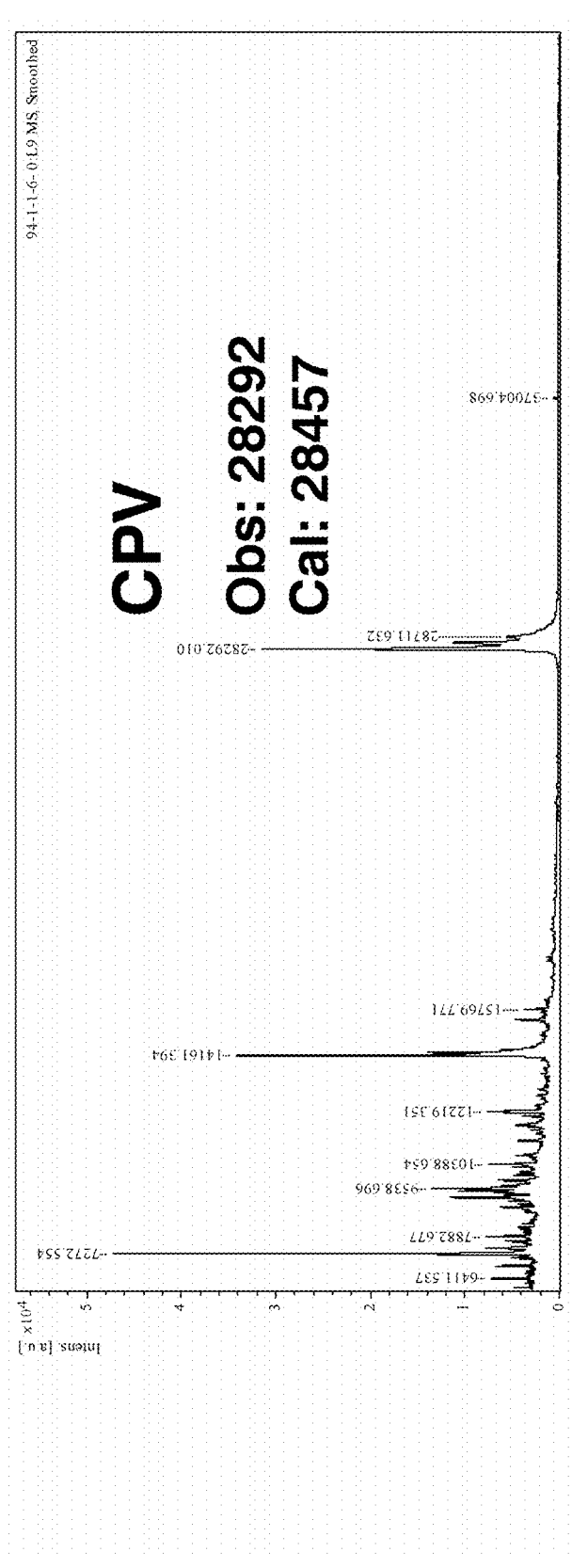
FIG. 4A is a graph showing the result of a MALDI-TOF MS analysis in Experimental Example 1.
Figure 4B:
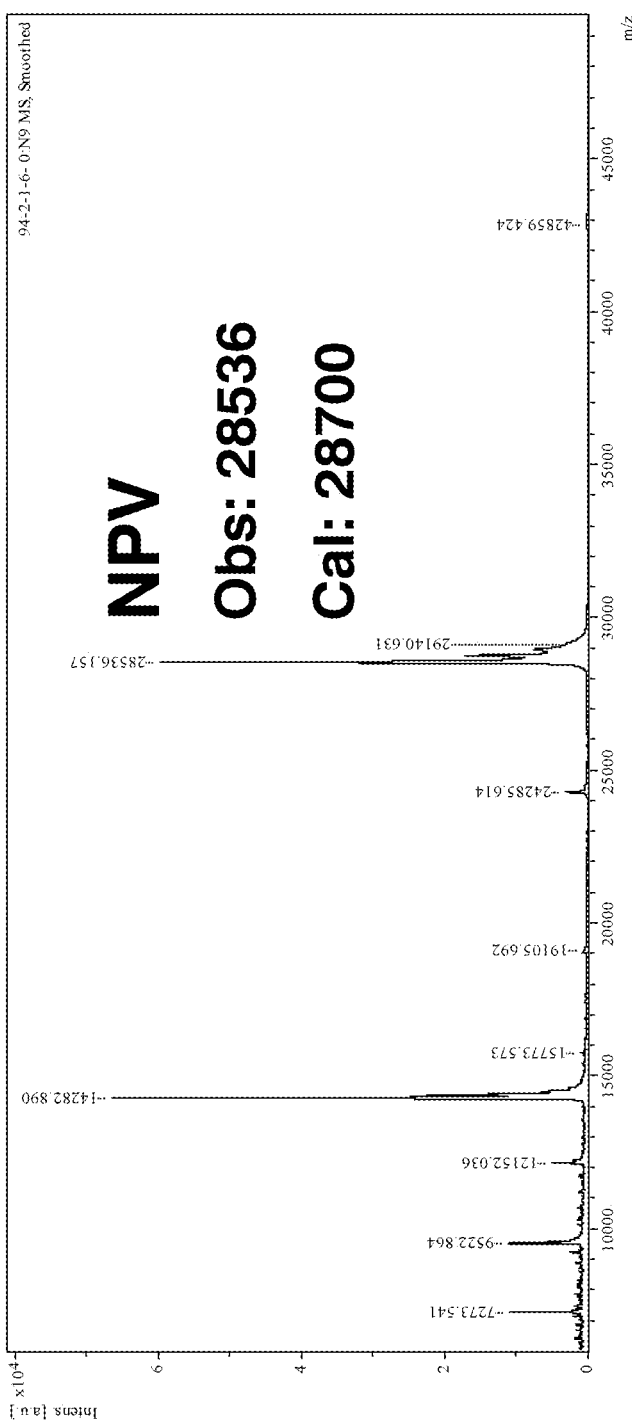
FIG. 4B is a graph showing the result of a MALDI-TOF MS analysis in Experimental Example 1.

FIGS. 4A and 4B are graphs showing the results of performing a MALDI-TOF MS analysis of the collected crystals of CPV-derived polyhedrin and the collected crystals of NPV-derived polyhedrin. FIG. 4A shows the result for CPV-derived polyhedrin, and FIG. 4B shows the result for NPV-derived polyhedrin. In FIGS. 4A and 4B, "Obs" denotes the measured molecular weight, and "Cal" denotes the predicted molecular weight of the full-length protein.

As a result, it was confirmed that the CPV-derived poly-hedrin and the NPV-derived polyhedrin have the predicted full-length molecular weights.

Experimental Example 2

(Crystallization of Protein in *Escherichia coli* 2)

CPV-derived polyhedrin variants were expressed in *Escherichia coli* in the same manner as in Experimental Example 1. Regarding the variants, a variant in which the 29th asparagine (N29) in the amino acid sequence set forth in SEQ ID NO:2 was substituted with serine (hereinafter, referred to as "N29S"; the amino acid sequence is set forth in SEQ ID NO:12), a variant including an amino acid sequence obtained by deleting the 192nd glycine (G192), the 193rd serine (5193), and the 194th alanine (A194) from the amino acid sequence set forth in SEQ ID NO:2 (hereinafter, referred to as "A3"; the amino acid sequence is set forth in SEQ ID NO:13), and a variant including an amino acid sequence obtained by deleting the 67th alanine (A67) to the 104th alanine (A104) from the amino acid sequence set forth in SEQ ID NO:3 (hereinafter, referred to as "A38"; the amino acid sequence is set forth in SEQ ID NO:1) were used. Genes encoding the CPV-derived polyhedrin variants were each inserted into a pET29b vector (Merck Millipore Corporation), and the expression vectors were produced. Subsequently, each of the expression vectors was used to transform *Escherichia coli* strain BL21.

Subsequently, each group of the transformed *Escherichia coli* was inoculated into 10 mL of LB medium and was cultured at 37° C. until the $OD_{600}$ reached 0.6 to 0.8. Subsequently, IPTG was added thereto so as to obtain a final concentration of 0.5 mM, and expression of the polyhedrin variants was induced. Subsequently, the cells were cultured at 30° C. for 20 to 24 hours, and crystals of the polyhedrin variants were formed.

Figure 5A:
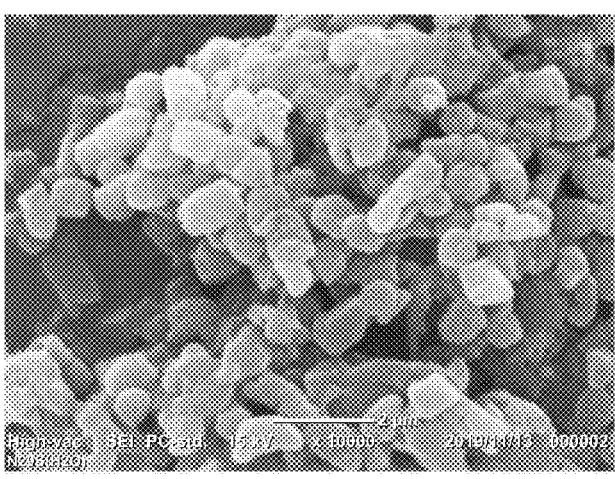
FIG. 5A is a photograph showing the result of observing crystals of a polyhedrin variant with a scanning electron microscope in Experimental Example 2.
Figure 5B:
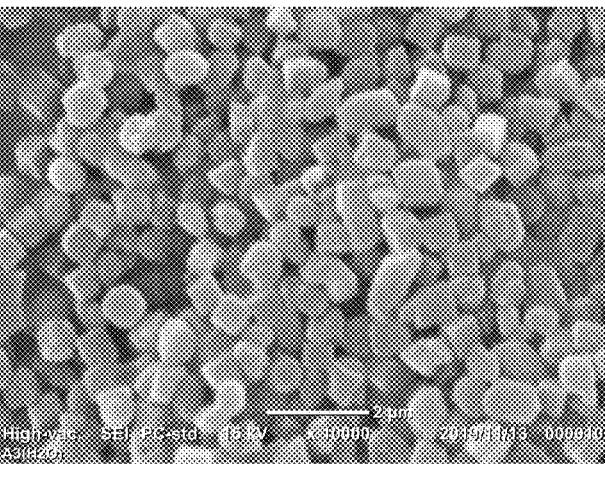
FIG. 5B is a photograph showing the result of observing crystals of a polyhedrin variant with a scanning electron microscope in Experimental Example 2.
Figure 5C:
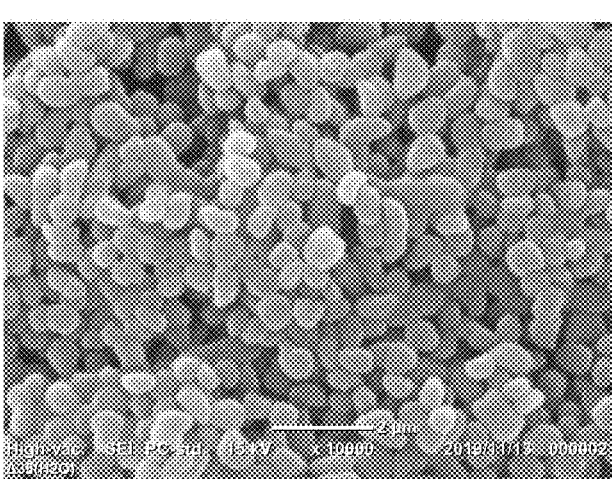
FIG. 5C is a photograph showing the result of observing crystals of a polyhedrin variant with a scanning electron microscope in Experimental Example 2.

Subsequently, each group of *Escherichia coli* was collected by centrifugation. Subsequently, *Escherichia coli* was ultrasonically crushed, and crystals of the polyhedrin variants were collected by centrifugation. FIGS. 5A to 5C are photographs showing the results of observing the crystals of the polyhedrin variants with a scanning electron microscope. FIG. 5A is a photograph showing the result of observing the crystals of the variant (N29S) with a scanning electron microscope, FIG. 5B is a photograph showing the result of observing the crystals of the variant (A3) with a scanning electron microscope, and FIG. 5C is a photograph showing the result of observing the crystals of the variant (A38) with a scanning electron microscope. In FIGS. 5A to 5C, the scale bar indicates 2 μm. As a result, crystals were observed in all the samples, and it was confirmed that crystals of the polyhedrin variants can be formed in *Escherichia coli*.

Figure 6A:
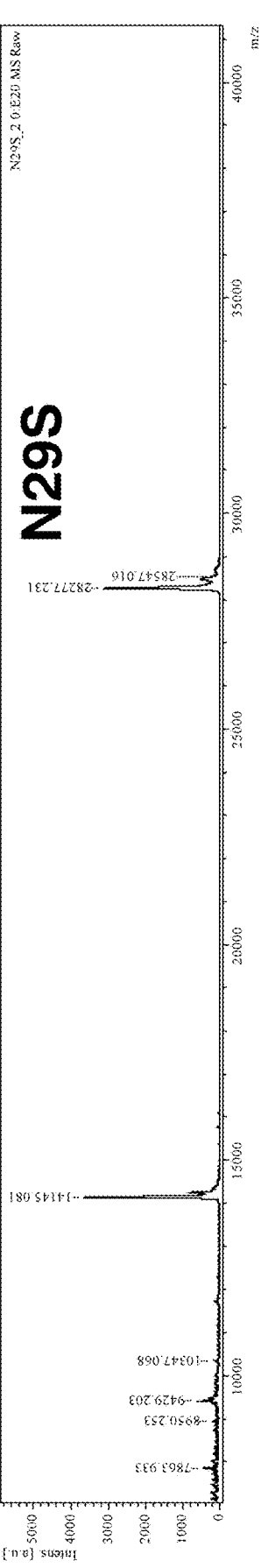
FIG. 6A is a graph showing the result of a MALDI-TOF MS analysis in Experimental Example 2.
Figure 6B:
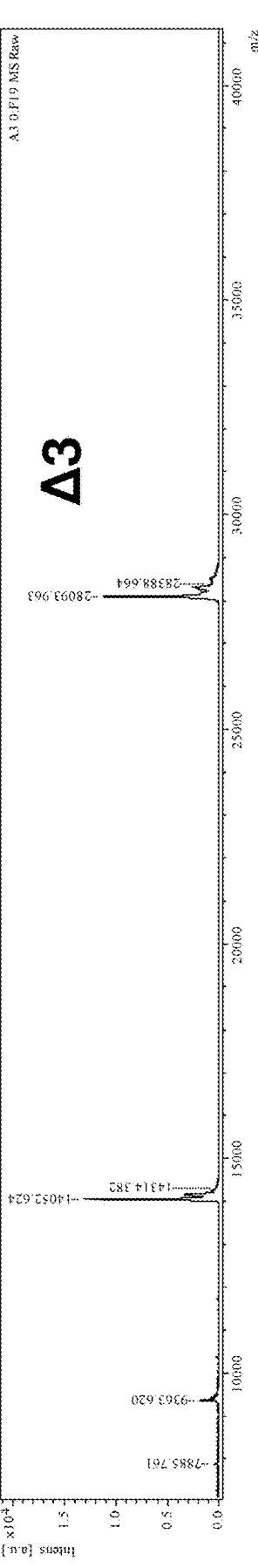
FIG. 6B is a graph showing the result of a MALDI-TOF MS analysis in Experimental Example 2.
Figure 6C:
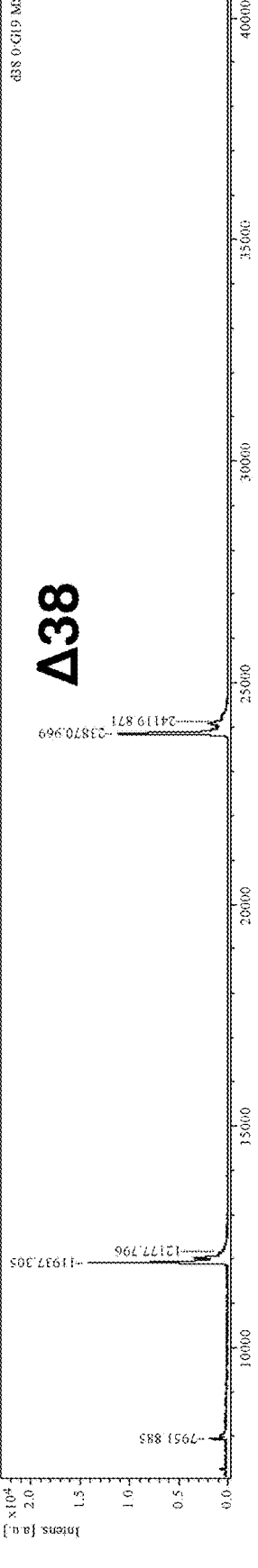
FIG. 6C is a graph showing the result of a MALDI-TOF MS analysis in Experimental Example 2.

FIGS. 6A to 6C are graphs showing the results of performing a MALDI-TOF MS analysis of the collected crystals of the polyhedrin variants. FIG. 6A shows the result for the variant (N29S), FIG. 6B shows the result for the variant (A3), and FIG. 6C shows the result for the variant (A38). As a result, it was confirmed that each of the polyhedrin variants had the predicted full-length molecular weight.

Experimental Example 3

(Crystallization of Protein in *Escherichia coli* 3)

CPV-derived polyhedrin (the amino acid sequence is set forth in SEQ ID NO:2) was expressed in *Escherichia coli* strain BL21 in the same manner as in Experimental Example 1, and crystals were formed. Here, the temperature of crystallization was set to 30° C. or 37° C.

Specifically, first, the transformed *Escherichia coli* was inoculated into 10 mL of LB medium and was cultured at 37° C. until the $OD_{600}$ reached 0.6 to 0.8. Subsequently, IPTG was added thereto so as to obtain a final concentration of 0.5 mM, and expression of the polyhedrin was induced. Subsequently, the cells were cultured at 30° C. or 37° C. for 20 to 24 hours, and crystals of polyhedrin were formed.

Figure 7A:
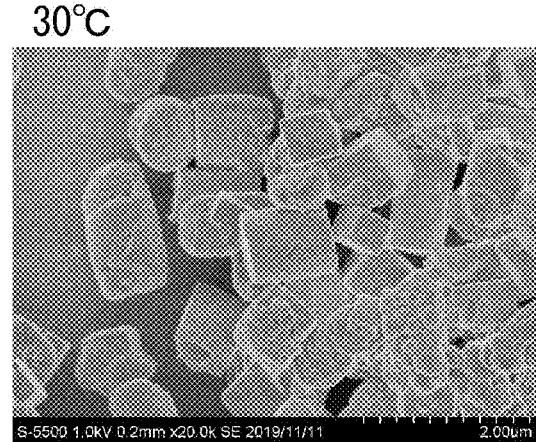
FIG. 7A is a photograph showing the result of observing crystals of polyhedrin with a scanning electron microscope in Experimental Example 3.
Figure 7B:
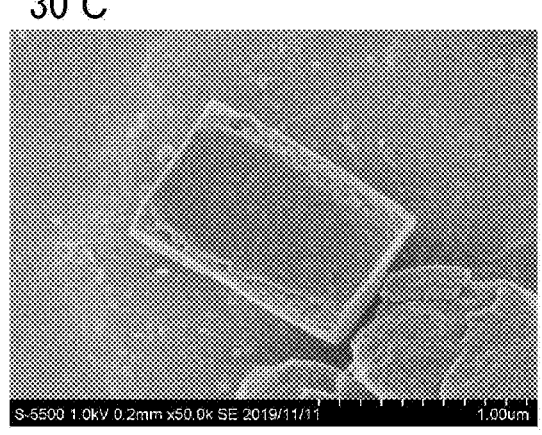
FIG. 7B is a photograph showing the result of observing crystals of polyhedrin with a scanning electron microscope in Experimental Example 3.
Figure 7C:
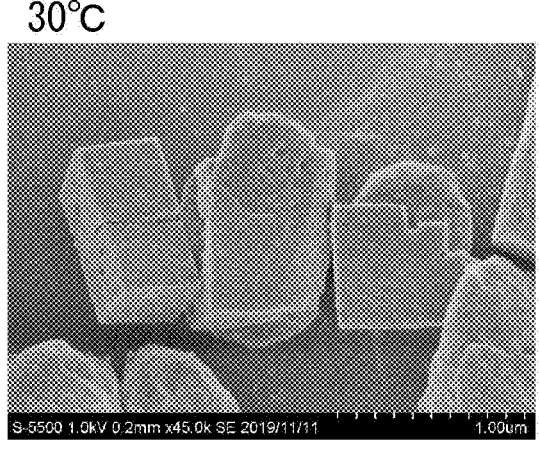
FIG. 7C is a photograph showing the result of observing crystals of polyhedrin with a scanning electron microscope in Experimental Example 3.
Figure 7D:
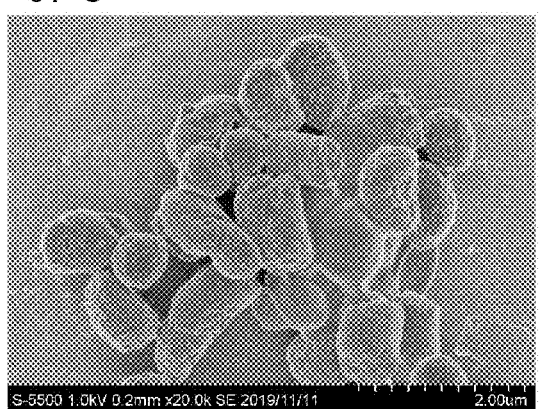
FIG. 7D is a photograph showing the result of observing crystals of polyhedrin with a scanning electron microscope in Experimental Example 3.
Figure 7E:
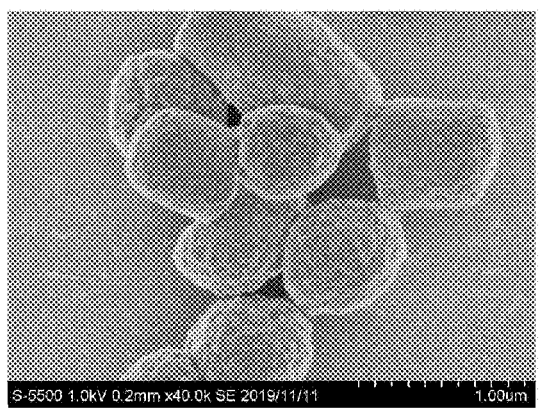
FIG. 7E is a photograph showing the result of observing crystals of polyhedrin with a scanning electron microscope in Experimental Example 3.
Figure 7F:
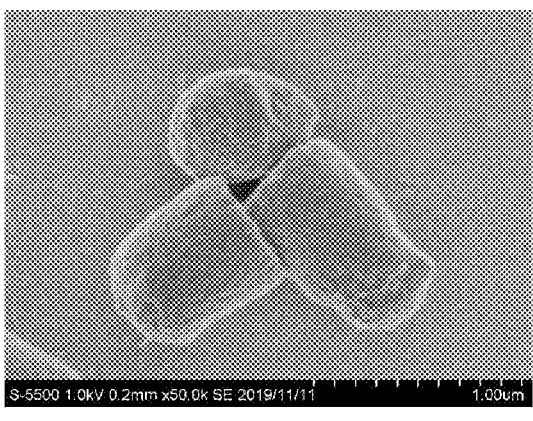
FIG. 7F is a photograph showing the result of observing crystals of polyhedrin with a scanning electron microscope in Experimental Example 3.

Subsequently, each group of *Escherichia coli* was collected by centrifugation. Subsequently, *Escherichia coli* was ultrasonically crushed, and crystals of polyhedrin were collected by centrifugation. FIGS. 7A to 7C are photographs showing the results of observing the crystals of polyhedrin crystallized at 30° C. with a scanning electron microscope. Furthermore, FIGS. 7D to 7F are photographs showing the results of observing the crystals of polyhedrin crystallized at 37° C. with a scanning electron microscope. As a result, it was clarified that polyhedrin can be crystallized at any temperature. In addition, a tendency was recognized that the quality of the crystals of polyhedrin is enhanced by performing crystallization at a lower temperature.

Experimental Example 4

(Structural Analysis of Crystals of Polyhedrin)

*Escherichia coli* strain BL21 having an expression vector of the CPV-derived polyhedrin (the amino acid sequence is set forth in SEQ ID NO:2) produced in Experimental Example 1 was inoculated into 10 mL of LB medium and was cultured at 37° C. until the $OD_{600}$ reached 0.6 to 0.8. Subsequently, IPTG was added thereto so as to obtain a final concentration of 0.5 mM, and expression of the polyhedrin was induced. Subsequently, the cells were cultured at 30° C. for 20 to 24 hours, and polyhedrin crystals were formed.

Figure 8:
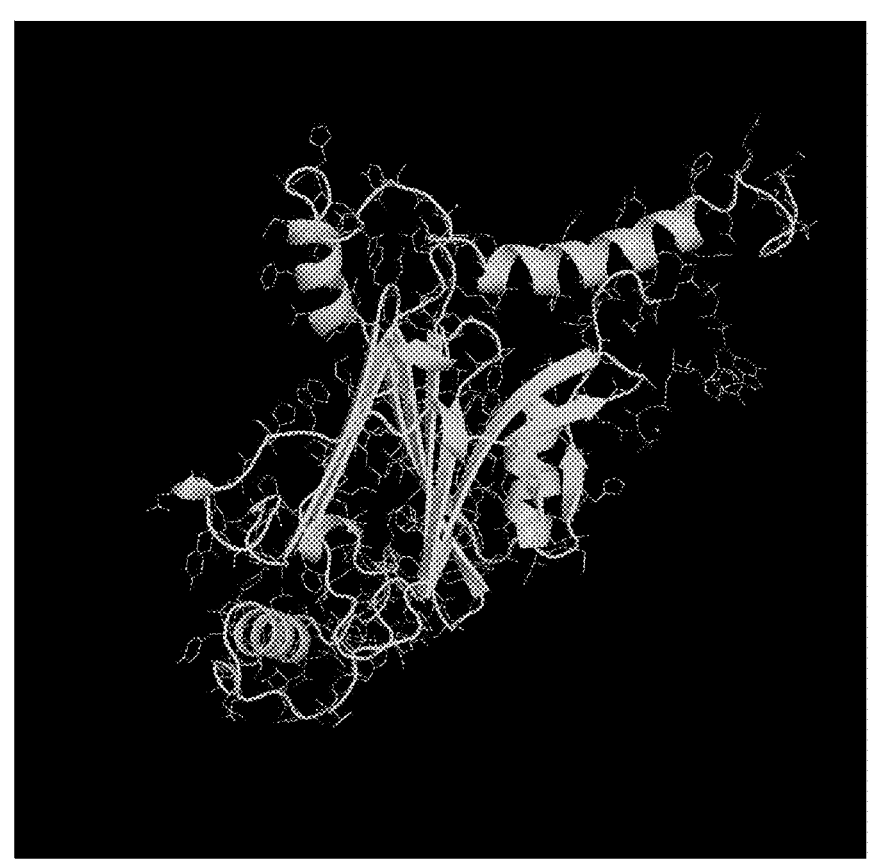
FIG. 8 is a diagram showing the result of subjecting the crystals of CPV-derived polyhedrin to a structural analysis as remaining in *Escherichia coli* in Experimental Example 4.

Subsequently, this *Escherichia coli* was subjected to X-ray crystal structure analysis together with the bacterial cells. For the X-ray crystal structure analysis, SPring-8 BL32XU was used. As a result, a structural analysis at a resolution of 1.8 Å was successfully achieved. FIG. 8 is a diagram showing the results of subjecting the crystals of CPV-derived polyhedrin to a structural analysis as remaining in *Escherichia coli*.

Subsequently, X-ray crystal structure analysis was carried out in the same manner as in Experimental Example 1, by using the crystals of polyhedrin purified from *Escherichia coli*. For the X-ray crystal structure analysis, SPring-8 BL32XU was used. For comparison, crystals of polyhedrin produced in insect cell strain Sf21 and purified were also similarly subjected to X-ray crystal structure analysis. As a result, a structural analysis of the purified crystals at a resolution of 1.9 Å was successfully achieved.

Figure 9A:
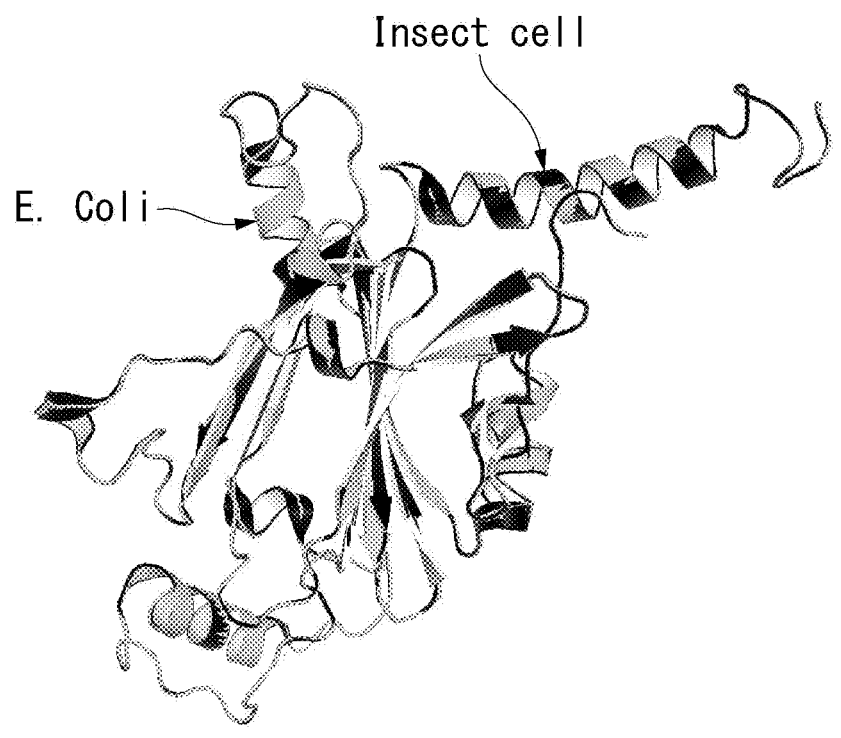
FIG. 9A is a diagram in which a three-dimensional structure of a crystal of polyhedrin produced by *Escherichia coli* and a three-dimensional structure of a crystal of polyhedrin produced by an insect cell are superimposed in Experimental Example 4.

FIG. 9A is a diagram in which the three-dimensional structure of a crystal of polyhedrin produced by *Escherichia coli* and the three-dimensional structure of a crystal of polyhedrin produced by the insect cells are superimposed. As a result, it was confirmed that the two coincide.

Figure 9B:
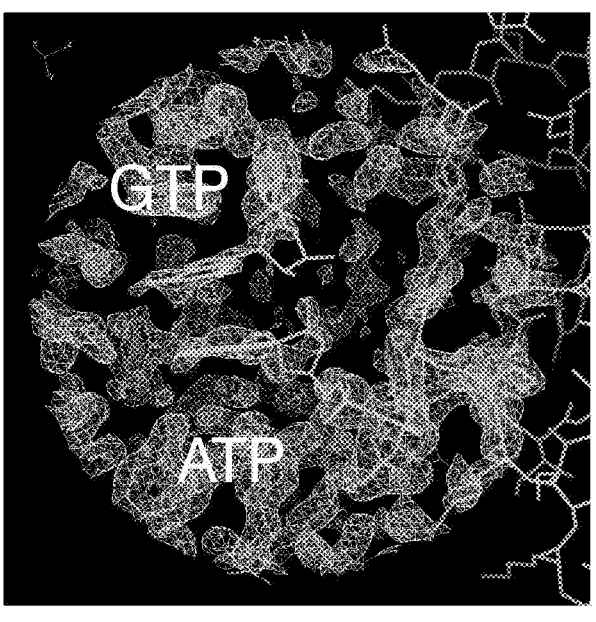
FIG. 9B is an image showing the result of a three-dimensional structural analysis of the crystals of polyhedrin produced by *Escherichia coli*.
Figure 9C:
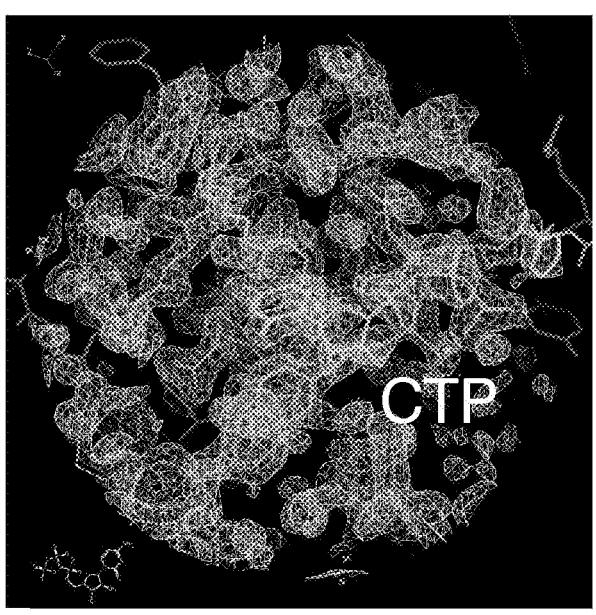
FIG. 9C is an image showing the result of a three-dimensional structural analysis of the crystals of polyhedrin produced by *Escherichia coli*.

FIGS. 9B and 9C are images showing the results of a three-dimensional structural analysis of the crystals of polyhedrin produced in *Escherichia coli*. In FIGS. 9B and 9C, "GTP" denotes guanosine triphosphate, "ATP" denotes adenosine triphosphate, and "CTP" denotes cytosine triphosphate. As a result, as shown in FIGS. 9B and 9C, it was confirmed that a nucleic acid is bound to the three-dimensional structure of the crystal of polyhedrin produced in *Escherichia coli*. This result further supports that the crystal of polyhedrin produced in *Escherichia coli* is equivalent to the crystal of polyhedrin produced in an insect cell.

Experimental Example 5

(Crystallization of Protein in *Escherichia coli* 4)

A gene encoding CPV-derived polyhedrin (the amino acid sequence is set forth in SEQ ID NO:2) was inserted into a pET29b vector (Merck Millipore Corporation), and an expression vector was produced. Furthermore, a gene encoding green fluorescent protein (sfGFP), which is a non-crystalline protein, was inserted into a pET21c vector (Merck Millipore Corporation), and an expression vector was produced.

sfGFP was used in the form of a fusion protein (the amino acid sequence is set forth in SEQ ID NO:15) of the H1 region of CPV-derived polyhedrin (the amino acid sequence is set forth in SEQ ID NO:14) and sfGFP. Subsequently, each of the expression vectors was mixed and used to transform *Escherichia coli* strain BL21.

Subsequently, the transformed *Escherichia coli* was inoculated into 10 mL of LB medium and was cultured at 37° C. until the $OD_{600}$ reached 0.6 to 0.8. Subsequently, IPTG was added thereto so as to obtain a final concentration of 0.5 mM, expression of the polyhedrin and sfGFP was induced, and the proteins were co-expressed. Subsequently, the transformed cells were cultured at 30° C. for 20 to 24 hours, and co-crystals of polyhedrin and sfGFP were formed.

Figure 10A:
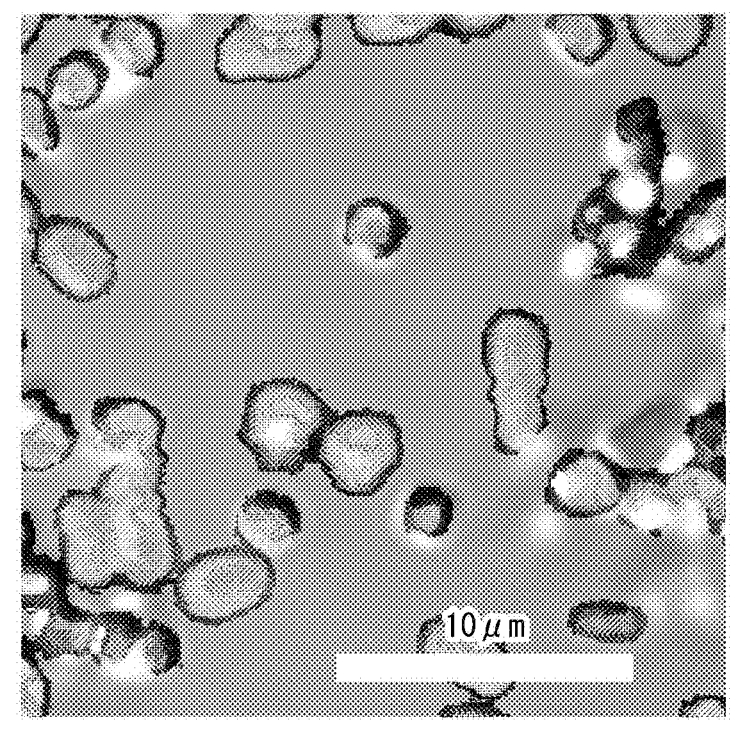
FIG. 10A is a confocal fluorescence microphotograph taken in Experimental Example 5.
Figure 10B:
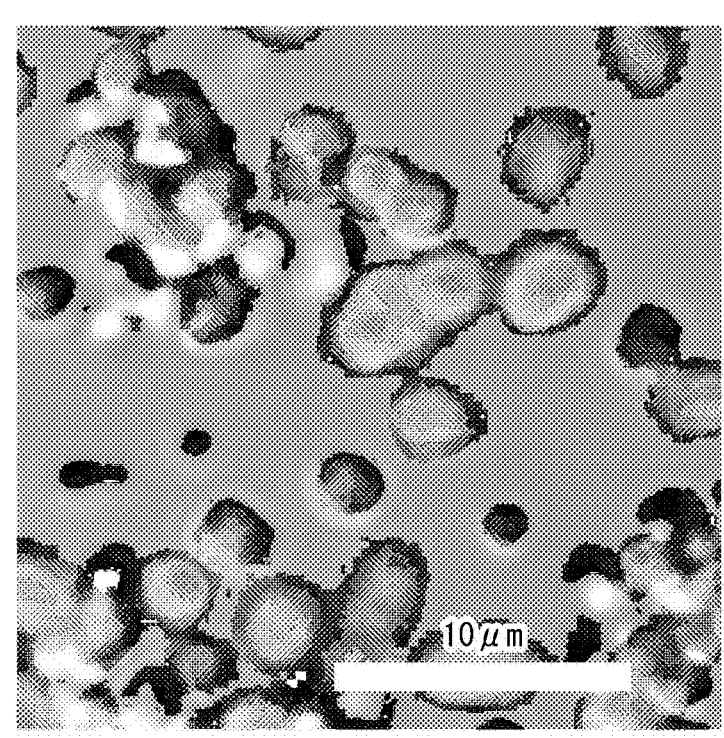
FIG. 10B is a confocal fluorescence microphotograph taken in Experimental Example 5.

Subsequently, each group of *Escherichia coli* was collected by centrifugation. Subsequently, *Escherichia coli* was ultrasonically crushed, and crystals of polyhedrin were collected by centrifugation. FIGS. 10A and 10B are representative photographs showing the results of observing co-crystals of polyhedrin and sfGFP crystallized at 30° C. with a confocal fluorescence microscope. In FIGS. 10A and 10B, a bright field image and a fluorescence image of sfGFP are superimposed and displayed. In FIGS. 10A and 10B, regions where the fluorescence of sfGFP was detected are indicated by dots.

As a result, it was confirmed that the formed crystals emit fluorescence of sfGFP. This result indicates that a co-crystal of polyhedrin and sfGFP was formed.

Experimental Example 6

(Structural Analysis of Crystals of Polyhedrin Variants)

An X-ray crystal structure analysis of the crystal of the CPV-derived polyhedrin variant (Δ3) and the crystal of the CPV-derived polyhedrin variant (Δ38), which were purified in Experimental Example 2, was performed. For the X-ray crystal structure analysis, SPring-8 BL32XU was used.

Figure 11A:
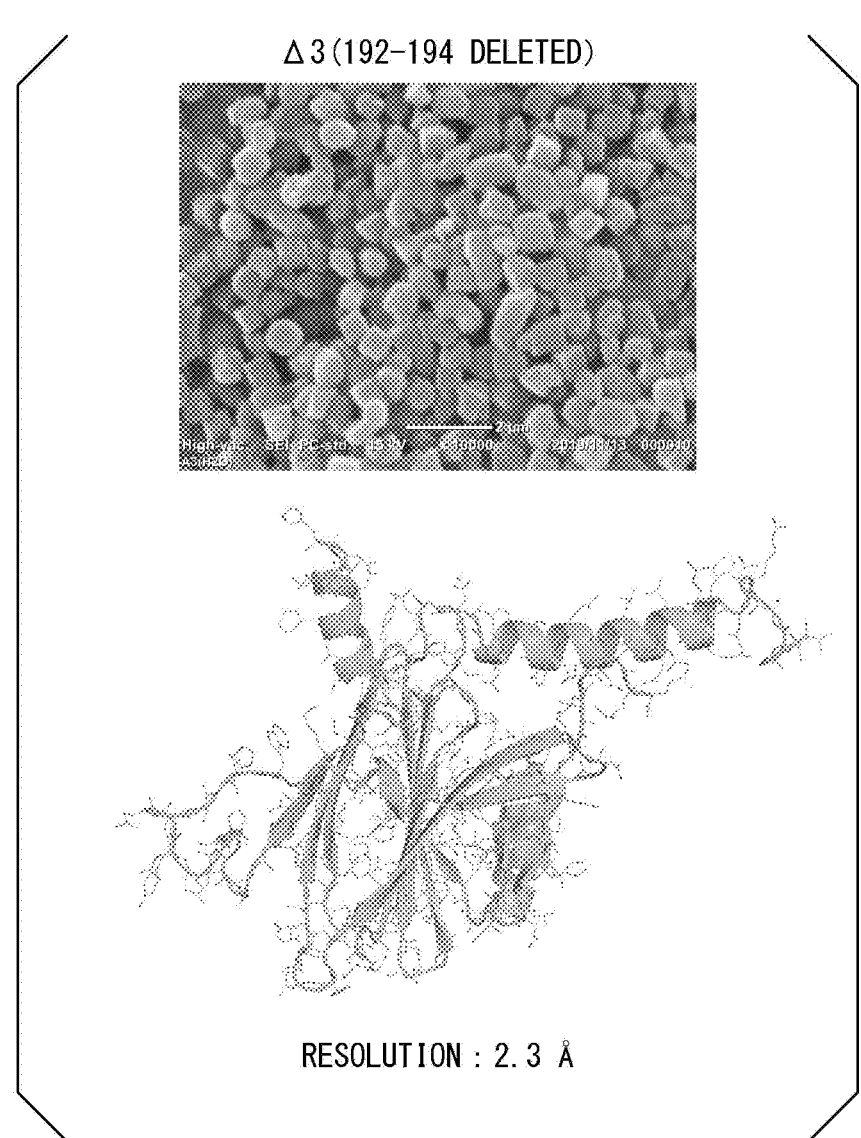
FIG. 11A upper part is a photograph showing the result of observing crystals of a polyhedrin variant with a scanning electron microscope in Experimental Example 6, and FIG. 11A lower part is a diagram showing the result of subjecting the crystals of the polyhedrin variant to a structural analysis.

FIG. 11A upper part is a photograph showing the result of observing the crystals of the variant (Δ3) with a scanning electron microscope, and FIG. 11A lower part is a diagram showing the result of a structural analysis of the crystal of the variant (Δ3). As a result, regarding the crystal of the purified variant (Δ3), a structural analysis at a resolution of 2.3 Å was successfully achieved.

Figure 11B:
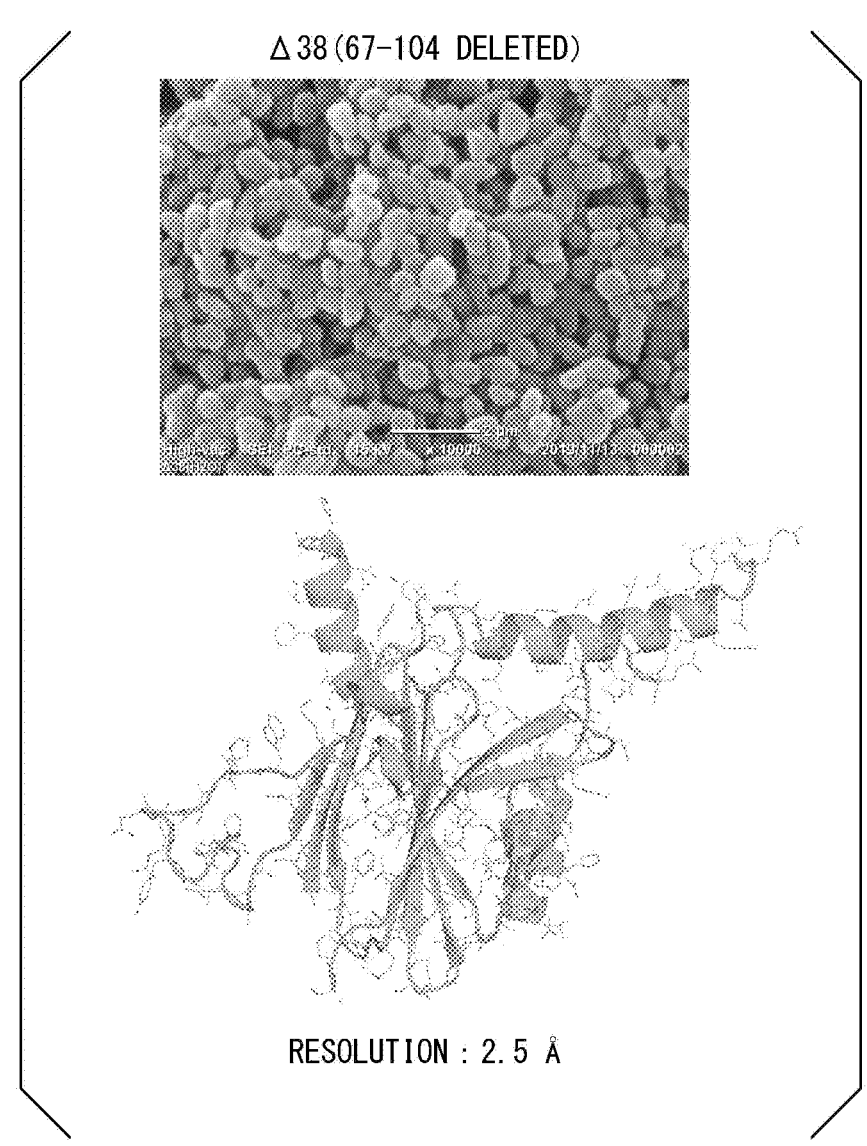
FIG. 11B upper part is a photograph showing the result of observing crystals of a polyhedrin variant with a scanning electron microscope in Experimental Example 6, and FIG. 11B lower part is a diagram showing the result of subjecting the crystals of the polyhedrin variant to a structural analysis.

Furthermore, FIG. 11B upper part is a photograph showing the result of observing the crystals of the variant (Δ38) with a scanning electron microscope, and FIG. 11B lower part is a diagram showing the result of a structural analysis of the crystal of the variant (Δ38). As a result, regarding the crystal of the purified variant (Δ38), a structural analysis at a resolution of 2.5 Å was successfully achieved.

Experimental Example 7

(Crystallization of Protein in *Escherichia coli* 5)

A gene encoding Crystalline inclusion protein A (CipA) was inserted into a pET29b vector (Merck Millipore Corporation), and an expression vector was produced. Subsequently, the expression vector was used to transform *Escherichia coli* strain BL21.

Figure 12A:
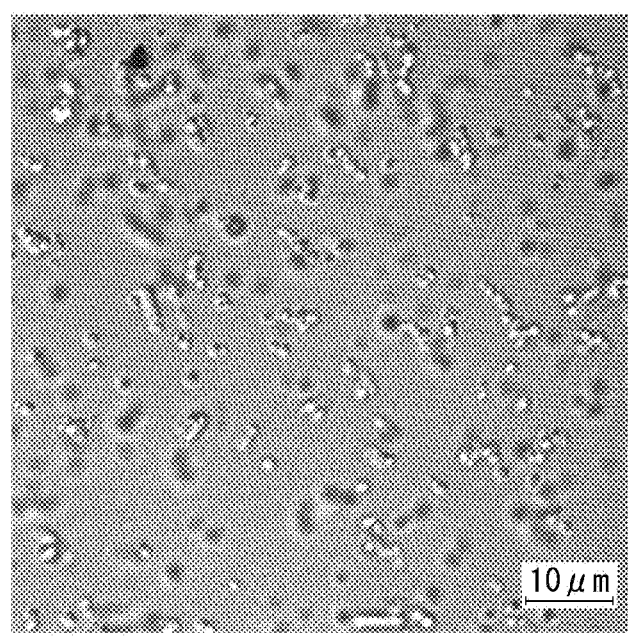
FIG. 12A is an optical microphotograph of *Escherichia coli* in which crystals of CipA were formed inside the bacterial cells in Experimental Example 7.

Subsequently, the transformed *Escherichia coli* was inoculated into 10 mL of LB medium and was cultured at 37° C. until the $OD_{600}$ reached 0.6 to 0.8. Subsequently, IPTG was added thereto so as to obtain a final concentration of 0.5 mM, and expression of CipA was induced. Subsequently, the transformed cells were cultured at 30° C. for 20 to 24 hours, and crystals of CipA were formed. FIG. 12A is an optical microphotograph of *Escherichia coli* in which crystals of CipA were formed inside the bacterial cells. The scale bar indicates 10 μm.

Figure 12B:
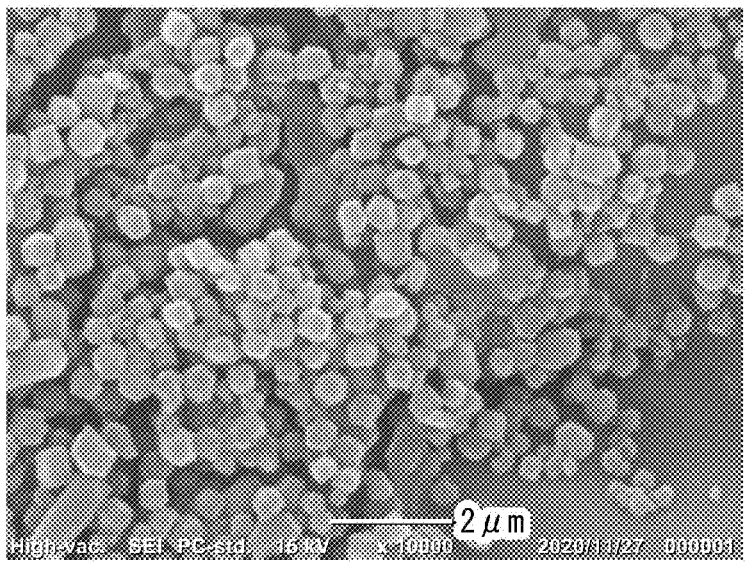
FIG. 12B is a photograph showing the result of observing the crystals of CipA with a scanning electron microscope in Experimental Example 7.

Subsequently, *Escherichia coli* was collected by centrifugation. Subsequently, *Escherichia coli* was ultrasonically crushed, and crystals of CipA were collected by centrifugation. FIG. 12B is a photograph showing the results of observing the crystals of CipA with a scanning electron microscope. The scale bar indicates 2 μm.

Subsequently, an X-ray crystal structure analysis of the purified crystals of CipA was performed. For the X-ray crystal structure analysis, SPring-8 BL32XU was used. As a result, diffraction data at a resolution of 2.8 Å could be acquired.

From the above-described results, it was clarified that crystals of CipA can be formed in *Escherichia coli*.

Experimental Example 8

(Crystallization of Protein in *Escherichia coli* 6)

A gene encoding a fusion protein of ubiquitin (hereinafter, may be referred to as "Ubq") and a cytoplasmic polyhedral protein (hereinafter, may be referred to as "PhM") was inserted into a pET29b vector (Merck Millipore Corporation), and an expression vector was produced.

Expression vectors were produced for two kinds of fusion proteins, namely, a fusion protein in which Ubq was located on the N-terminal side (hereinafter, may be referred to as "Ubq-PhM") and a fusion protein in which PhM was located on the N-terminal side (hereinafter, may be referred to as "PhM-Ubq"). In both of Ubq-PhM and PhM-Ubq, a linker "GGGS (SEQ ID NO:18)" was inserted between Ubq and PhM. An amino acid sequence of Ubq-PhM is set forth in SEQ ID NO:19, and an amino acid sequence of PhM-Ubq is set forth in SEQ ID NO:20.

Subsequently, each of the expression vectors was used to transform *Escherichia coli* strain BL21. Subsequently, each group of the transformed *Escherichia coli* was inoculated into 10 mL of LB medium and was cultured at 37° C. until the $OD_{600}$ reached 0.6 to 0.8. Subsequently, IPTG was added thereto so as to obtain a final concentration of 0.5 mM, and expression of both Ubq-PhM and PhM-Ubq was induced. Subsequently, the transformed cells were cultured at 30° C. for 20 to 24 hours, and crystals of both Ubq-PhM and PhM-Ubq were formed.

Figure 13A:
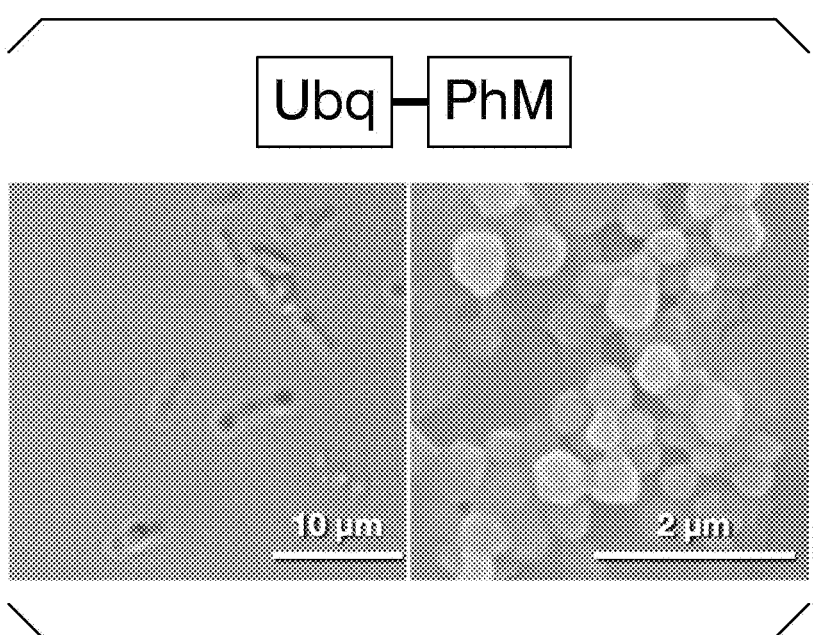
FIG. 13A left part is an optical microphotograph of *Escherichia coli* in which crystals of fusion proteins were formed inside the bacterial cells in Experimental Example 7.
Figure 13B:
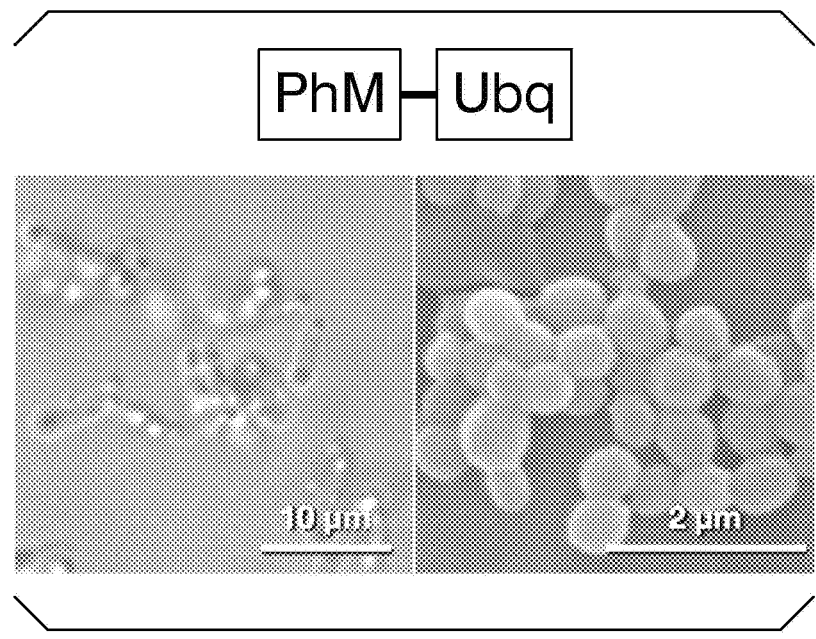
FIG. 13B left part is an optical microphotograph of *Escherichia coli* in which crystals of fusion proteins were formed inside the bacterial cells in Experimental Example 7.

FIG. 13A left part is an optical microphotograph of *Escherichia coli* in which crystals of Ubq-PhM were formed inside the bacterial cells, and FIG. 13B left part is an optical microphotograph of *Escherichia coli* in which crystals of PhM-Ubq were formed inside the bacterial cells. The scale bar indicates 10 μm.

Subsequently, each group of *Escherichia coli* was collected by centrifugation. Subsequently, each group of *Escherichia coli* was ultrasonically crushed, and crystals of each of Ubq-PhM and PhM-Ubq were collected by centrifugation. FIG. 13A right part is a photograph showing the result of observing the crystals of Ubq-PhM with a scanning electron microscope, and FIG. 13B right part is a photograph showing the result of observing the crystals of PhM-Ubq with a scanning electron microscope. The scale bar indicates 2 μm.

Figure 13C:
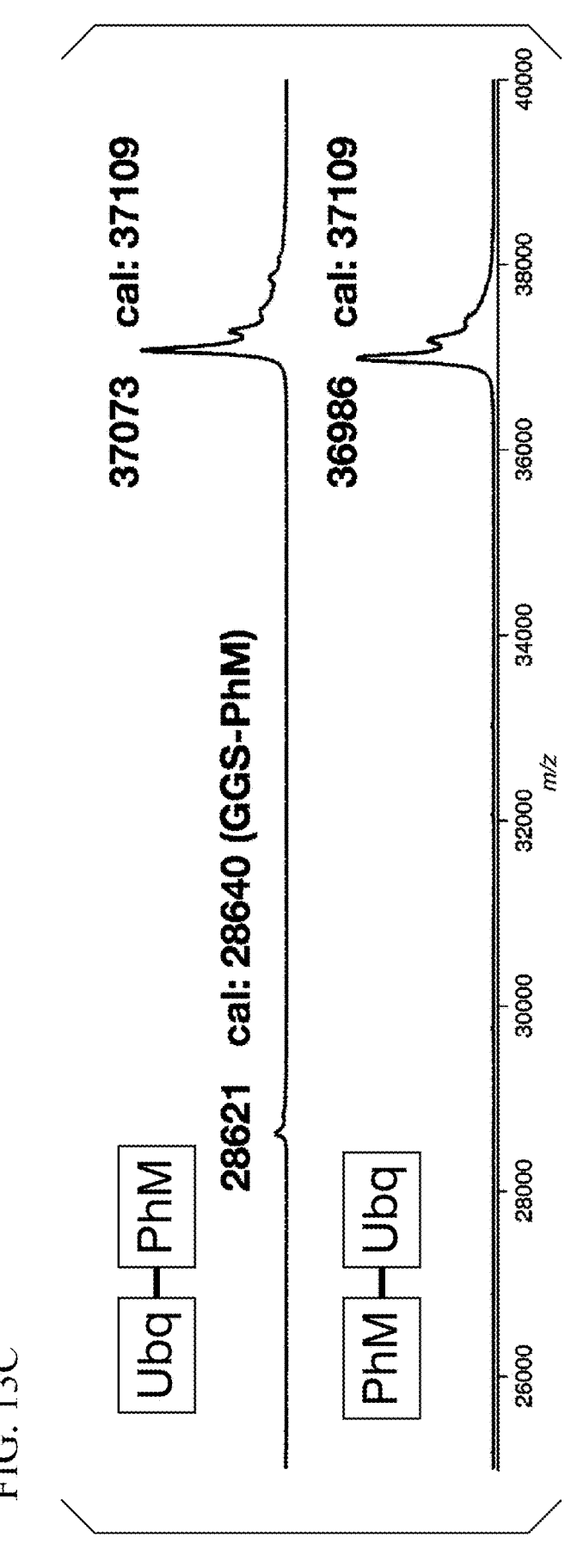
FIG. 13C is a graph showing the result of performing a MALDI-TOF MS analysis of the collected crystals of the fusion proteins in Experimental Example 7.

FIG. 13C is a graph showing the results of performing a MALDI-TOF MS analysis of each of the collected crystals of Ubq-PhM and PhM-Ubq. FIG. 13C upper part shows the result for Ubq-PhM, and FIG. 13C lower part shows the result for PhM-Ubq. In FIG. 13C, "Cal" denotes the predicted molecular weight of each of the fusion proteins. As a result, it was confirmed that each of Ubq-PhM and PhM-Ubq had the predicted molecular weight.

From the above-described results, it was clarified that crystals of Ubq-PhM and PhM-Ubq can be formed in *Escherichia coli.*

Experimental Example 9

(Crystallization of Protein in *Escherichia coli* 7)

A gene encoding a fusion protein of green fluorescent protein (hereinafter, may be referred to as "GFP") and a cytoplasmic polyhedral protein (hereinafter, may be referred to as "PhM") was inserted into a pET29b vector (Merck Millipore Corporation), and an expression vector was produced.

In the produced fusion protein, a linker "GGGS (SEQ ID NO:18)" was inserted between GFP and PhM, where GFP was located on the N-terminal side (hereinafter, may be referred to as "GFP-PhM"). The amino acid sequence of GFP-PhM is set forth in SEQ ID NO:21.

Subsequently, the expression vector was used to transform *Escherichia coli* strain BL21. Subsequently, the transformed *Escherichia coli* was inoculated into 10 mL of LB medium and was cultured at 37° C. until the $OD_{600}$ reached 0.6 to 0.8. Subsequently, IPTG was added thereto so as to obtain a final concentration of 0.5 mM, and expression of GFP-PhM was induced. Subsequently, the transformed cells were cultured at 30° C. for 20 to 24 hours, and crystals of GFP-PhM were each formed.

Subsequently, *Escherichia coli* was collected by centrifugation. Subsequently, *Escherichia coli* was ultrasonically crushed, and crystals of GFP-PhM were collected by centrifugation.

Figure 14A:
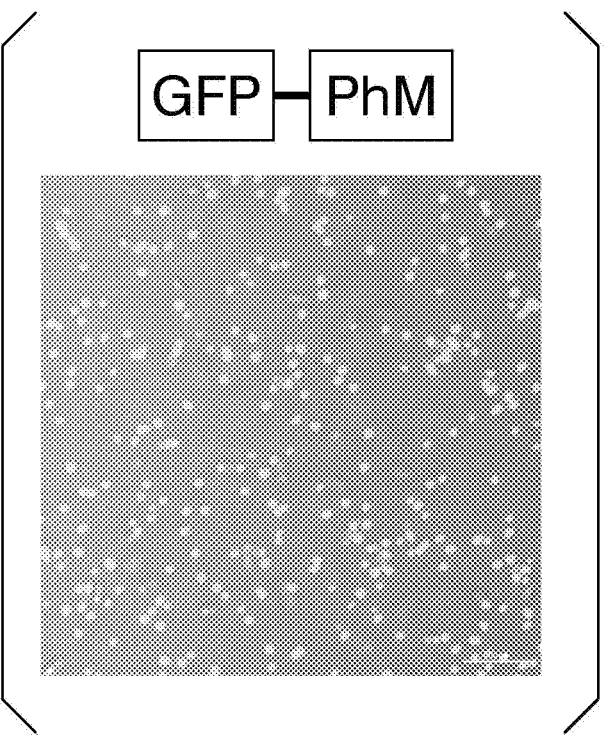
FIG. 14A is an image obtained by merging an optical microphotograph of crystals of a fusion protein formed inside the bacterial cells of *Escherichia coli* and collected in Experimental Example 9, with a photograph obtained by observing fluorescence of GFP.
Figure 14B:
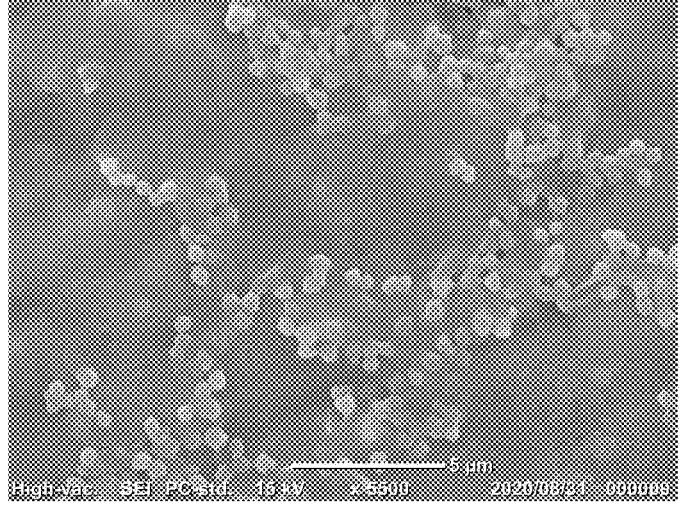
FIG. 14B is a photograph showing the result of observing the crystals of the fusion protein with a scanning electron microscope in Experimental Example 9.

FIG. 14A is an image obtained by merging an optical microphotograph of the collected crystals of GFP-PhM with a photograph obtained by observing the fluorescence of GFP. The scale bar indicates 10 μm. FIG. 14B is a photograph showing the result of observing the crystals of GFP-PhM with a scanning electron microscope. The scale bar indicates 5 μm.

Figure 14C:
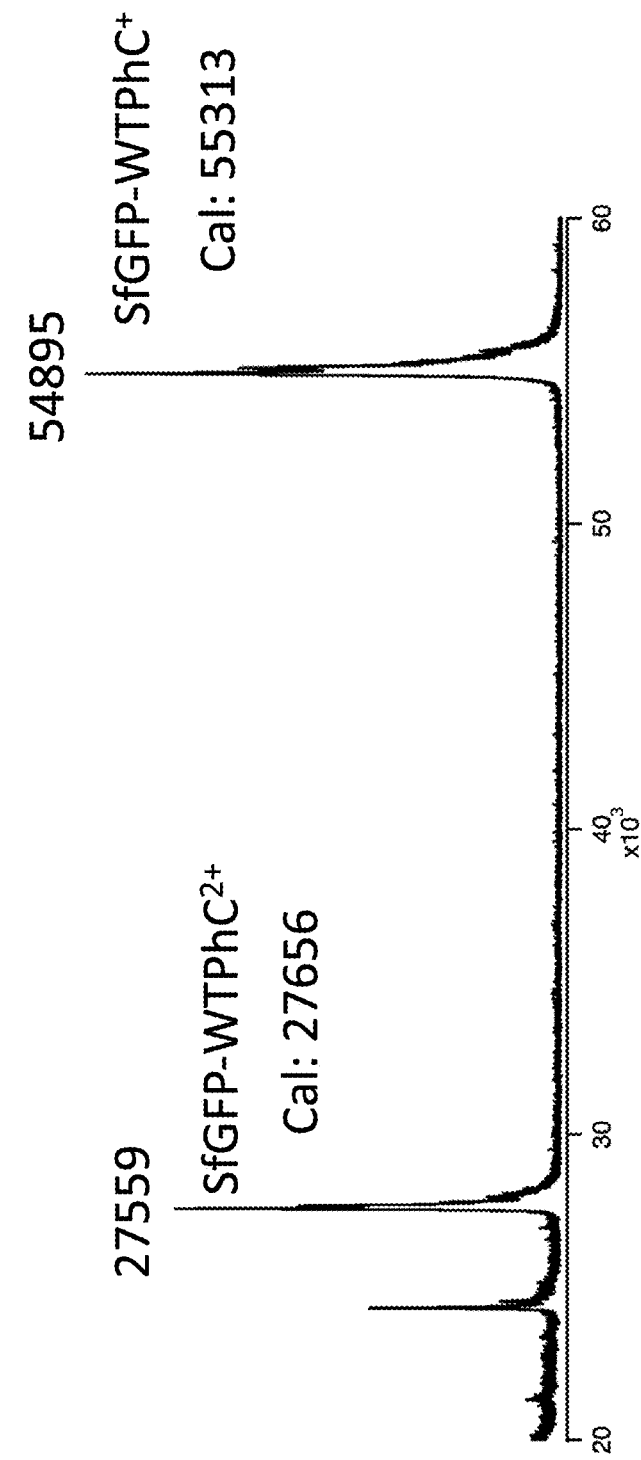
FIG. 14C is a graph showing the result of performing a MALDI-TOF MS analysis of the collected crystals of the fusion protein in Experimental Example 9.

FIG. 14C is a graph showing the result of performing a MALDI-TOF MS analysis of the collected crystals of GFP-PhM. In FIG. 14C, "SfGFP-WTPhC²⁺" denotes a divalent ion of SfGFP-WTPhC (GFP-PhM), and "SfGFP-WTPhC⁺" denotes a monovalent ion of SfGFP-WTPhC (GFP-PhM). Furthermore, "Cal" denotes the predicted molecular weight of the fusion protein. As a result, it was confirmed that GFP-PhM has the predicted molecular weight.

From the above-described results, it was clarified that crystals of GFP-PhM can be formed in *Escherichia coli.*

Experimental Example 10

(Crystallization of Protein in *Escherichia coli* 8)

A gene encoding a fusion protein of a thalidomide-binding domain (hereinafter, may be referred to as "TBD") of cereblon (CRBN) protein and a cytoplasmic polyhedral protein (hereinafter, may be referred to as "PhM") was inserted into a pET29b vector (Merck Millipore Corporation), and an expression vector was produced.

Expression vectors were produced for the two kinds of fusion proteins, namely, a fusion protein in which TBD was located on the N-terminal side (hereinafter, may be referred to as "TBD-PhM") and a fusion protein in which PhM was located on the N-terminal side (hereinafter, may be referred to as "PhM-TBD"). In both of TBD-PhM and PhM-TBD, a linker "GGGS (SEQ ID NO:18)" was inserted between TBD and PhM. An amino acid sequence of TBD-PhM is set forth in SEQ ID NO:22, and an amino acid sequence of PhM-TBD is set forth in SEQ ID NO:23.

Subsequently, each of the expression vectors was used to transform *Escherichia coli* strain BL21. Subsequently, each group of the transformed *Escherichia coli* was inoculated into 10 mL of LB medium and was cultured at 37° C. until the $OD_{600}$ reached 0.6 to 0.8. Subsequently, IPTG was added thereto so as to obtain a final concentration of 0.5 mM, and expression of both TBD-PhM and PhM-TBD was induced. Subsequently, the transformed cells were cultured at 30° C. for 20 to 24 hours, and crystals of both TBD-PhM and PhM-TBD were formed.

Subsequently, each group of *Escherichia coli* was collected by centrifugation. Subsequently, each group of *Escherichia coli* was ultrasonically crushed, and crystals of each of TBD-PhM and PhM-TBD were collected by centrifugation.

Figure 15A:
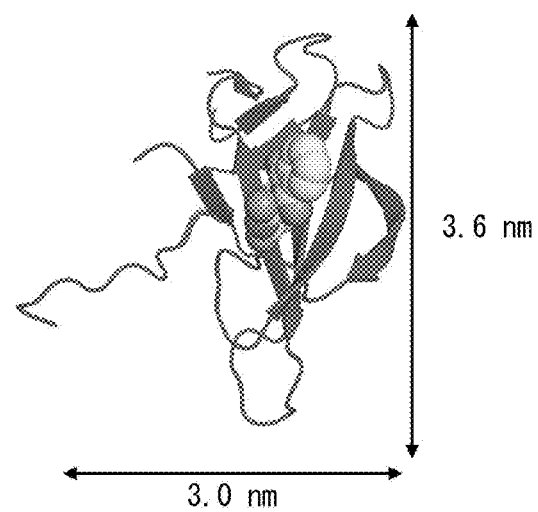
FIG. 15A is a diagram showing a three-dimensional structure of a thalidomide-binding domain of CRBN protein.
Figure 15B:
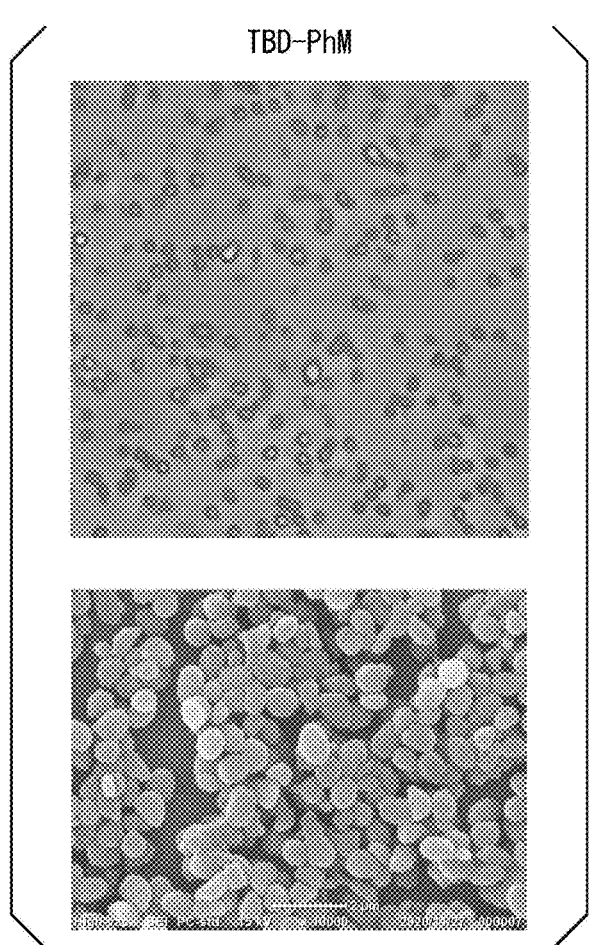
FIG. 15B upper part is an optical microphotograph of crystals of fusion proteins synthesized and collected in *Escherichia coli* in Experimental Example 10.
Figure 15C:
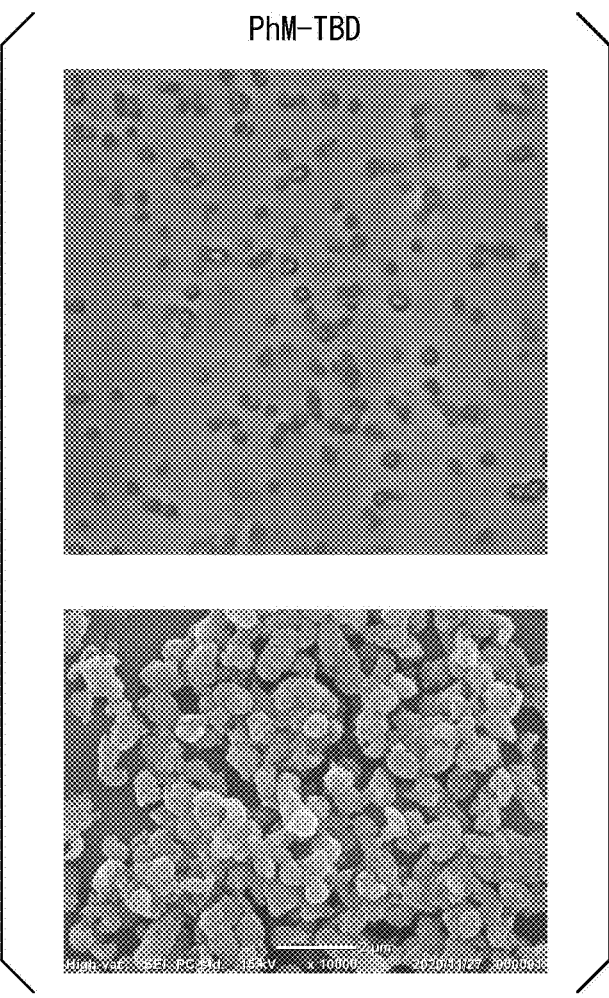
FIG. 15C upper part is an optical microphotographs of crystals of fusion proteins synthesized and collected in *Escherichia coli* in Experimental Example 10.

FIG. 15A is a diagram showing a three-dimensional structure of TBD (thalidomide-binding domain of CRBN protein). FIG. 15B upper part is an optical microphotograph of the collected crystals of TBD-PhM, and FIG. 15C upper part is an optical microphotograph of the collected crystals of PhM-TBD. Furthermore, FIG. 15B lower part is a photograph showing the result of observing the crystals of TBD-PhM with a scanning electron microscope, and FIG. 15C lower part is a photograph showing the result of observing the crystals of PhM-TBD with a scanning electron microscope. The scale bar indicates 2 μm.

From the above-described results, it was clarified that crystals of TBD-PhM and PhM-TBD can be formed in *Escherichia coli.*

Experimental Example 11

(Crystallization of Protein in *Escherichia coli* 9)

A gene encoding a fragment of a cytoplasmic polyhedral protein was inserted into a pET29b vector (Merck Millipore Corporation), and an expression vector was produced.

As the fragment of the cytoplasmic polyhedral protein, expression vectors were produced for four kinds of fragments, namely, a fragment consisting of the 1st to 114th amino acids of the amino acid sequence of the cytoplasmic polyhedral protein set forth in SEQ ID NO:2 (hereinafter, may be referred to as "fragment 1: M1 to S114"), a fragment consisting of the 1st to 155th amino acids of the amino acid sequence of SEQ ID NO:2 (hereinafter, may be referred to as "fragment 2: M1 to R155"), a fragment consisting of the 116th to 248th amino acids of the amino acid sequence of SEQ ID NO:2 (hereinafter, may be referred to as "fragment 3: S116 to Q248"), and a fragment consisting of the 58th to 248th amino acids of the amino acid sequence of SEQ ID NO:2 (hereinafter, may be referred to as "fragment 4: K58 to Q248").

An amino acid sequence of fragment 1: M1 to S114 is set forth in SEQ ID NO:24, an amino acid sequence of fragment 2: M1 to R155 is set forth in SEQ ID NO:25, an amino acid sequence of fragment 3: S116 to Q248 is set forth in SEQ ID NO:26, and an amino acid sequence of fragment 4: K58 to Q248 is set forth in SEQ ID NO:27.

Subsequently, each of the expression vectors was used to transform *Escherichia coli* strain BL21. Subsequently, each group of the transformed *Escherichia coli* was inoculated into 10 mL of LB medium and was cultured at 37° C. until the OD$_{600}$ reached 0.6 to 0.8. Subsequently, IPTG was added thereto so as to obtain a final concentration of 0.5 mM, and expression of each of the fragment 1 to fragment 4 was induced. Subsequently, the transformed cells were cultured at 30° C. for 20 to 24 hours, and each of the crystals of the fragment 1 to fragment 4 was formed.

Figure 16A:
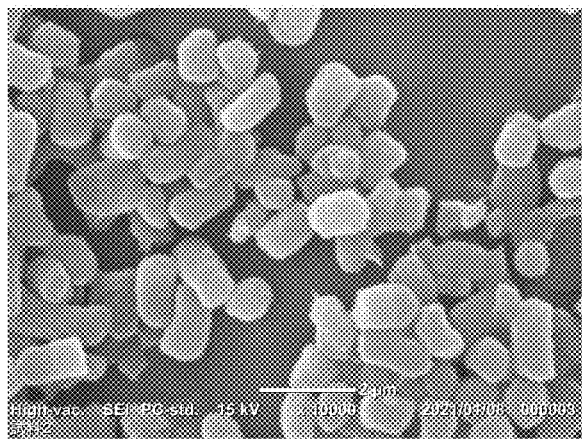
FIG. 16A is a photograph showing the result of observing crystals of fragments of cytoplasmic polyhedral proteins with a scanning electron microscope in Experimental Example 11.

Subsequently, each group of *Escherichia coli* was collected by centrifugation. Subsequently, each group of *Escherichia coli* was ultrasonically crushed, and crystals of the fragment 1 to fragment 4 were each collected by centrifugation. FIG. 16A is a photograph showing the result of observing the crystals of fragment 1: M1 to S114 with a scanning electron microscope, and FIG. 16C is a photograph showing the result of observing the crystals of fragment 2: M1 to R155 with a scanning electron microscope. The scale bar indicates 2 µm.

Figure 17A:
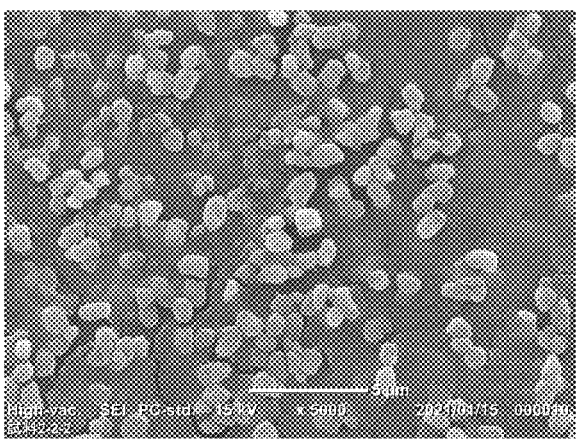
FIG. 17A is a photograph showing the result of observing crystals of fragments of cytoplasmic polyhedral proteins with a scanning electron microscope in Experimental Example 11.
Figure 17B:
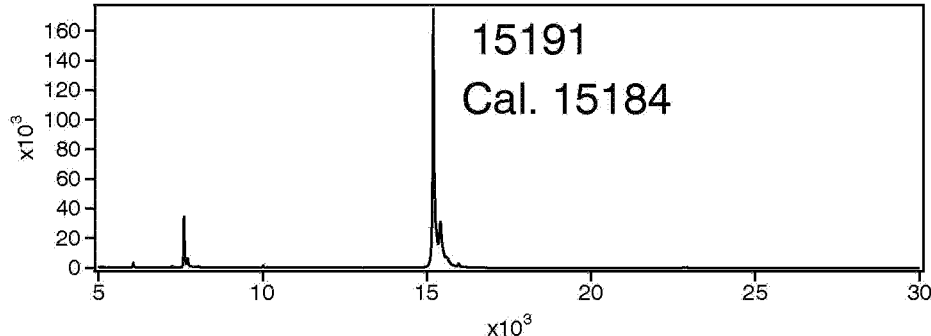
FIG. 17B is a graph showing the result of performing a MALDI-TOF MS analysis of the collected crystals of the fragments of the cytoplasmic polyhedral proteins in Experimental Example 11.
Figure 17C:
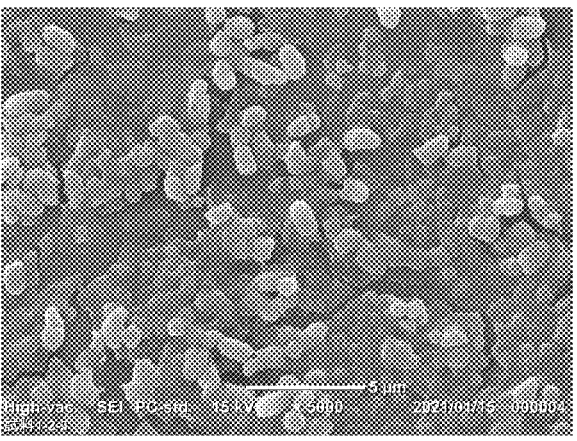
FIG. 17C is a photograph showing the result of observing crystals of fragments of cytoplasmic polyhedral proteins with a scanning electron microscope in Experimental Example 11.
Figure 17D:
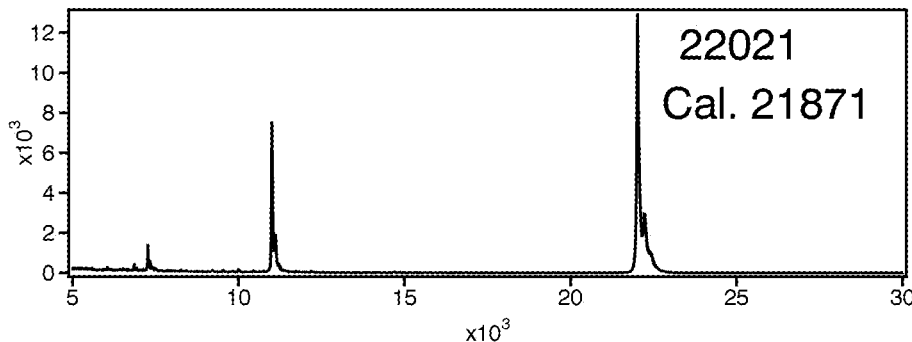
FIG. 17D is a graph showing the result of performing a MALDI-TOF MS analysis of the collected crystals of the fragments of the cytoplasmic polyhedral proteins in Experimental Example 11.

Furthermore, FIG. 17A is a photograph showing the result of observing the crystals of fragment 3: S116 to Q248 with a scanning electron microscope, and FIG. 17C is a photograph showing the result of observing the crystals of fragment 4: K58 to Q248 with a scanning electron microscope. The scale bar indicates 5 µm. Furthermore, FIG. 16B is a graph showing the result of performing a MALDI-TOF MS analysis of the collected crystals of fragment 1: M1 to S114, FIG. 16D is a graph showing the result of performing a MALDI-TOF MS analysis of the collected crystals of fragments 2: M1 to R155, FIG. 17B is a graph showing the result of performing a MALDI-TOF MS analysis of the collected crystals of fragment 3: S116 to Q248, and FIG. 17D is a graph showing the result of performing a MALDI-TOF MS analysis of the collected crystals of fragment 4: K58 to Q248. In FIG. 16 and FIG. 17, "Cal" denotes the predicted molecular weight of each fragment. As a result, it was confirmed that each of the fragment 1 to the fragment 4 has the predicted molecular weight.

From the above-described results, it was clarified that crystals of fragments of a cytoplasmic polyhedral protein can be formed in *Escherichia coli*.

INDUSTRIAL APPLICABILITY

According to the present invention, a technology for conveniently producing a crystal of a protein can be provided.

The invention claimed is:

1. A crystal structure analysis method, comprising:

inducing expression of a crystalline protein in *Escherichia coli* into which an expression construct of the crystalline protein has been introduced, and incubating the *Escherichia coli* for a predetermined time until a crystal of the crystalline protein is formed inside the *Escherichia coli*, subjecting the crystal to an X-ray crystal structure analysis together with the *Escherichia coli* and determining the crystal structure at an Å level, wherein the crystalline protein is a protein according to any one of the following (i) to (iii):

(i) a cytoplasmic polyhedral protein, a nuclear polyhedral protein, Crystalline inclusion protein A (CipA) or Crystalline inclusion protein B (CipB);

(ii) a protein consisting of an amino acid sequence in which 1 to 50 amino acids have been deleted, substituted, or added in an amino acid sequence of the protein of (i) and having a crystal-forming ability; and (iii) a fusion protein of the protein of (i) or (ii) and a target peptide of 5 to 50 amino acids.

2. The crystal structure analysis method according to claim 1, wherein the crystalline protein is a fusion protein comprising a target peptide of 5 to 50 amino acids inserted between the 66th amino acid and the 67th amino acid of an amino acid sequence set forth in SEQ ID NO:1, or between an amino acid corresponding to the 66th amino acid of the amino acid sequence set forth in SEQ ID NO: 1 and an amino acid corresponding to the 67th amino acid thereof in an amino acid sequence of a protein including an amino acid sequence in which one amino acid or a plurality of amino acids have been deleted, substituted, or added in the amino acid sequence set forth in SEQ ID NO:1 and having a crystal-forming ability.

3. The crystal structure analysis method according to claim 1, wherein the predetermined time is 3 to 30 hours.

4. The crystal structure analysis method according to claim 1, wherein the incubating is carried out at 18° C. to 40° C.

* * * * *